(12) United States Patent
Kumar et al.

(10) Patent No.: US 11,998,651 B2
(45) Date of Patent: Jun. 4, 2024

(54) SKIN PREPARATION APPLICATOR

(71) Applicant: Becton, Dickinson and Company, Franklin Lakes, NJ (US)

(72) Inventors: Manish Kumar, Arrah (IN); Karthik M R, Bangalore (IN); Balaji Kannan, Chennai (IN); Prasad Govindaraj, Coimbatore (IN); Shishir Prasad, Ramsey, NJ (US); Kevin M. Ryan, Whitehouse Station, NJ (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 152 days.

(21) Appl. No.: 17/697,499

(22) Filed: Mar. 17, 2022

(65) Prior Publication Data

US 2023/0293749 A1  Sep. 21, 2023

(51) Int. Cl.
*A61L 2/18* (2006.01)
*A61L 2/26* (2006.01)
*B05C 1/00* (2006.01)
*B05C 11/10* (2006.01)
*B05C 17/005* (2006.01)
*F16K 15/14* (2006.01)

(52) U.S. Cl.
CPC ............... *A61L 2/18* (2013.01); *A61L 2/26* (2013.01); *B05C 1/00* (2013.01); *B05C 11/1026* (2013.01); *A61L 2202/15* (2013.01); *B05C 17/005* (2013.01); *B05C 17/00503* (2013.01); *F16K 15/147* (2013.01)

(58) Field of Classification Search
CPC .......... A61L 2/18; A61L 2/26; A61L 2202/15; F16K 15/147; F16K 15/14; B05C 1/00; B05C 11/1026; B05C 17/005; B05C 17/00503; B05C 17/00583; B05C 17/00586; B05C 17/00593
USPC .................................................. 401/132–135
See application file for complete search history.

(56) References Cited

U.S. PATENT DOCUMENTS

| 5,435,660 | A | 7/1995 | Wirt | |
| 7,261,701 | B2 * | 8/2007 | Davis | A61M 35/006 604/289 |
| 8,956,065 | B2 | 2/2015 | Froimson | |
| 9,016,967 | B2 | 4/2015 | Law | |
| 9,802,439 | B2 * | 10/2017 | Albenge | B43K 8/12 |

* cited by examiner

*Primary Examiner* — David J Walczak
(74) *Attorney, Agent, or Firm* — Servilla Whitney LLC

(57) ABSTRACT

Fluid applicators with precise volume dispensing control for dispensing fluids such as a disinfectant in a controlled manner. Such fluid applicators may include a barrel including a sidewall having an inside surface defining a chamber for retaining a fluid, an end press, a push rod disposed within the chamber, the push rod having a push button and a piercing tip, a cap attached to a port via a hinge to cover a hydrophobic filter disposed on the sidewall of the chamber, a one-way valve disposed on the outlet on a distal end of the barrel, a disinfectant disposed within the chamber; a housing having a base and an open proximal end; and a fluid applicator sponge disposed in the base of the housing. An alternate fluid may include a deformable end press, a plurality of volume scale markings on an outer surface of the barrel, a push rod, a one-way valve and applicator sponge.

20 Claims, 21 Drawing Sheets

SKIN PREPARATION APPLICATOR

TECHNICAL FIELD

The present disclosure relates to fluid applicators, and in particular the present disclosure relates to a fluid applicator with precise volume dispensing control for dispensing fluids such as a disinfectant or antimicrobial agent in a controlled manner to achieve effective and optimal skin disinfection.

BACKGROUND

Fluid applicators are commonly used in the art to dispense disinfectant solution onto a patient's skin prior to or after medical procedures such as surgery or even when inserting an intravenous catheter or other vascular access device. Such devices are effective at locally disinfecting and reducing microbial infection of the surgical site ultimately to reduce the risk of bloodstream infections following the procedure.

Clinicians prefer quick release of disinfectant and reduced activation times for disinfection devices. For example, clinicians often complain of disinfection sponges taking longer periods of time for sponge to get wet with disinfectant post activation.

Fluid applicators within the art lack precise control of the release of disinfectant. The clinician performing the procedure has to estimate the volume of disinfecting solution necessary to adequately cover the surface area for a given procedure. In doing this estimation, clinicians will often choose to dispense an excess amount of fluid to ensure full wet-out of the skin as opposed to rounding-down to a smaller volume, which could lead to not completely wetting out the area and hence not fully disinfected areas. Alternatively, estimation of volume may lead to dispensing an excess amount of disinfectant or antimicrobial agent. Inconsistent dispensing rate of disinfecting agent may lead to inconsistent scrubbing that is stopped too early for effective cleaning.

An excess amount of fluid dispensed can lead to longer drying times, excessive disinfecting solution tackiness in the work area, and/or pooling and dripping from the target disinfecting area. These drips can run onto sterile field drapes, down the sides of the patient, and onto the clinician's gloves and clothing. Dripping, in conjunction with the fact that the disinfecting solution is often sticky (such as for Chlorhexidine), can cause parts of the clinician's gloves, foreign matter or bacterial contaminates sticking to the sterile draping areas where the solution dripped onto. In addition, pooling and dripping of the fluid takes significantly more time to dry, and allowing time for the fluid to dry is an extremely important requirement. The fluid is typically a disinfectant solution often containing 70% IPA, which is flammable if pooled. The pooled fluid can ignite by static electricity discharge from draping materials or by tools which are used for medical procedures such as laser surgery tools.

Some of the most common type of fluid applicators are dispensing devices having a breakable ampoule or cartridge containing disinfectant. The dispensing device can have a chamber for receiving the ampoule, an applicator head and a means for breaking the ampoule, thusly ejecting disinfectant onto the applicator head. To select a greater volume of disinfectant for greater surfaces areas which require disinfection, a larger ampoule can be selected. In operation, the clinician will break the ampoule resulting in rapid and uncontrolled gushing of the fluid from the ampoule. The fluid will first dispense at a higher rate and will dispense at a lesser rate as the ampoule empties.

Clinicians will often attempt to adjust for the variable rate by scrubbing faster (essentially covering more area faster) than otherwise recommended and then stopping scrubbing before the required minimum scrub time for a given disinfection procedure or required by the stated device instructions for the particular ampoule and applicator. Because the scrubbing and disinfecting is stopped before the minimum required time, or because there is no fluid remaining for the minimum required time, the skin area may not be fully or adequately disinfected, leading to potential increased risk of infection.

Due to the rapid and uncontrolled gushing of fluid upon breakage of an ampoule, common applicators have implemented various configurations to limit or control the flow of fluid. To overcome the challenges faced by clinicians, fluid applicators can be provided with additional ampoules of varying volume sizes available for the clinician to choose from. However, this solution results in fluid applicator kits with additional or excess ampoules, many of which will be discarded. Furthermore, it can be a challenge for the clinician to estimate which exact volume is needed due to unknown factors such as skin abortion of the disinfection solution and calculation of skin surface area due to complicated skin surface geometry, and time constraints of the given procedure. Further configurations can include means of limiting the flow of fluid downstream from the ampoule. Such means can include tortuous paths or absorbent materials which allow the gushing fluid to slowly permeate through the tortuous paths or absorbent materials before exiting the common applicator. This results in the clinician having to wait for the initial fluid to pass through the tortuous paths or absorbent materials in order to wet-out the bottom of the common applicator, resulting in a time delay between breakage of the ampoule and application of the disinfectant fluid.

Positive control of disinfectant release in the hand of user would eliminate such current issues complaints with respect to disinfection devices currently on the market.

In addition, current products in the market may seek overcome some of the aforementioned problems with high-cost solutions such as timers and gating mechanisms resulting in high costs of manufacturing and high retail costs per device.

Thus, there is a need to provide a low-cost fluid applicator which can provide a volume and flow control of disinfectant to allow for controlled and constant flow rate of fluid onto a scrubbing sponge of the applicator to allow clinicians to achieve improved efficacy of treatment and workflow.

SUMMARY

A first aspect of the present disclosure relates to a fluid applicator having a barrel including a sidewall having an inside surface defining a chamber for retaining a fluid, an open proximal end, a distal end including an elongate tip extending distally therefrom having a passageway therethrough in fluid communication with said chamber and an outlet on the distal end of the barrel. An end press is disposed on the open proximal end to fluidly seal the open proximal end of the barrel. A push rod is disposed within the chamber of the barrel, the push rod having a push button disposed on a proximal end of the push rod adjacent to the end press and a piercing tip disposed on a distal end of the push rod. In one or more embodiments, the end press is attached internally to the push rod.

A port is mounted on the sidewall of the barrel. In one or more embodiments, the port includes at least one side wall having an inside surface defining a compartment. In one or more embodiments, the port is configured as a collar.

A hydrophobic filter is disposed within the port on the sidewall of the chamber, the hydrophobic filter being in fluid communication with the chamber. In one or more embodiments, the compartment of the port surrounds the hydrophobic filter.

A cap is attached to the port via a hinge. In one or more embodiments, the hinge opens between a fully closed position to a fully open position of at least 120 degrees. In one or more embodiments, the hinge is a living hinge.

A one-way valve is disposed on the outlet on the distal end of the barrel. The one-way valve may be a duckbill valve, an umbrella valve, a ball-check valve, diaphragm check valve, swing check valve, stop-check valve, lift-check valve or a combination thereof. In one or more embodiments, the one-way valve is a duckbill valve.

A disinfectant is disposed within the chamber between the one-way valve and the end press. In one or more embodiments, the disinfectant or antimicrobial agent is selected from the group consisting essentially of isopropyl alcohol, ethanol, 2-propanol, butanol, methylparaben, ethylparaben, propylparaben, propyl gallate, butylated hydroxyanisole (BHA), butylated hydroxytoluene, t-butyl-hydroquinone, chloroxylenol, chlorhexidine, chlorhexidine diacetate, chlorohexidine gluconate, povidone iodine, alcohol, dichlorobenzyl alcohol, dehydroacetic acid, hexetidine, triclosan, hydrogen peroxide, colloidal silver, benzethonium chloride, benzalkonium chloride, octenidine, antibiotic, and mixtures thereof.

A housing having a base and an open proximal end is at the distal end of the barrel and a fluid applicator sponge is disposed in the base of the housing. The one-way valve partially extends into the base of the housing and is embedded into the fluid applicator sponge. In one or more embodiments, the tip and the one-way valve are positioned a distance from the open proximal end of the housing.

In one or more embodiments, the fluid applicator sponge is configured to uniformly distribute disinfectant released from the one-way valve.

In one or more embodiments, the barrel is at an angle relative to the housing.

In one or more embodiments, the barrel, port, push rod, push button or cap are made of a polypropylene or polyethylene material.

In one or more embodiments, the fluid applicator of the first aspect of the present disclosure includes volume scale markings on an outer surface of the barrel.

A second aspect of the present disclosure relates to a fluid applicator having a barrel including a sidewall having an inside surface defining a chamber for retaining a fluid, an open proximal end, a distal end including an elongate tip extending distally therefrom having a passageway therethrough in fluid communication with said chamber, an outlet on the distal end of the barrel and a plurality of volume scale markings on an outer surface of the barrel. A deformable end press is disposed on the open proximal end to fluidly seal the open proximal end of the barrel. The end press made of elastomeric material, e.g. thermoset rubber, thermoplastic vulcanizate, or thermoplastic elastomers.

A push rod is disposed within the chamber of the barrel, the push rod having a push button disposed on a proximal end of the push rod adjacent to the end press and a piercing tip disposed on a distal end of the push rod. In one or more embodiments, the end press is attached internally to the push rod.

A one-way valve is disposed on the outlet on the distal end of the barrel. The one-way valve may be a duckbill valve, an umbrella valve, a ball-check valve, diaphragm check valve, swing check valve, stop-check valve, lift-check valve or a combination thereof. In one or more embodiments, the one-way valve is a duckbill valve.

A disinfectant or antimicrobial agent is disposed within the chamber between the one-way valve and the end press. In one or more embodiments, the disinfectant or antimicrobial agent is selected from the group consisting essentially of isopropyl alcohol, ethanol, 2-propanol, butanol, methylparaben, ethylparaben, propylparaben, propyl gallate, butylated hydroxyanisole (BHA), butylated hydroxytoluene, t-butyl-hydroquinone, chloroxylenol, chlorhexidine, chlorhexidine diacetate, chlorohexidine gluconate, povidone iodine, alcohol, dichlorobenzyl alcohol, dehydroacetic acid, hexetidine, triclosan, hydrogen peroxide, colloidal silver, benzethonium chloride, benzalkonium chloride, octenidine, antibiotic, and mixtures thereof. In one or more embodiments, the disinfectant or antimicrobial agent is a fluid or a gel.

A housing having a base and an open proximal end is at the distal end of the barrel and a fluid applicator sponge is disposed in the base of the housing. The one-way valve partially extends into the base of the housing and is embedded into the fluid applicator sponge. In one or more embodiments, the tip and the one-way valve are positioned a distance from the open proximal end of the housing.

In one or more embodiments, the fluid applicator sponge is configured to uniformly distribute disinfectant released from the one-way valve.

In one or more embodiments, the barrel is at an angle relative to the housing.

In one or more embodiments, the barrel, port, push rod, push button or cap are made of a polypropylene or polyethylene material.

In one or more embodiments, the fluid applicator of the first aspect of the present disclosure includes volume scale markings on an outer surface of the barrel.

DETAILED DESCRIPTION

Figure 1:
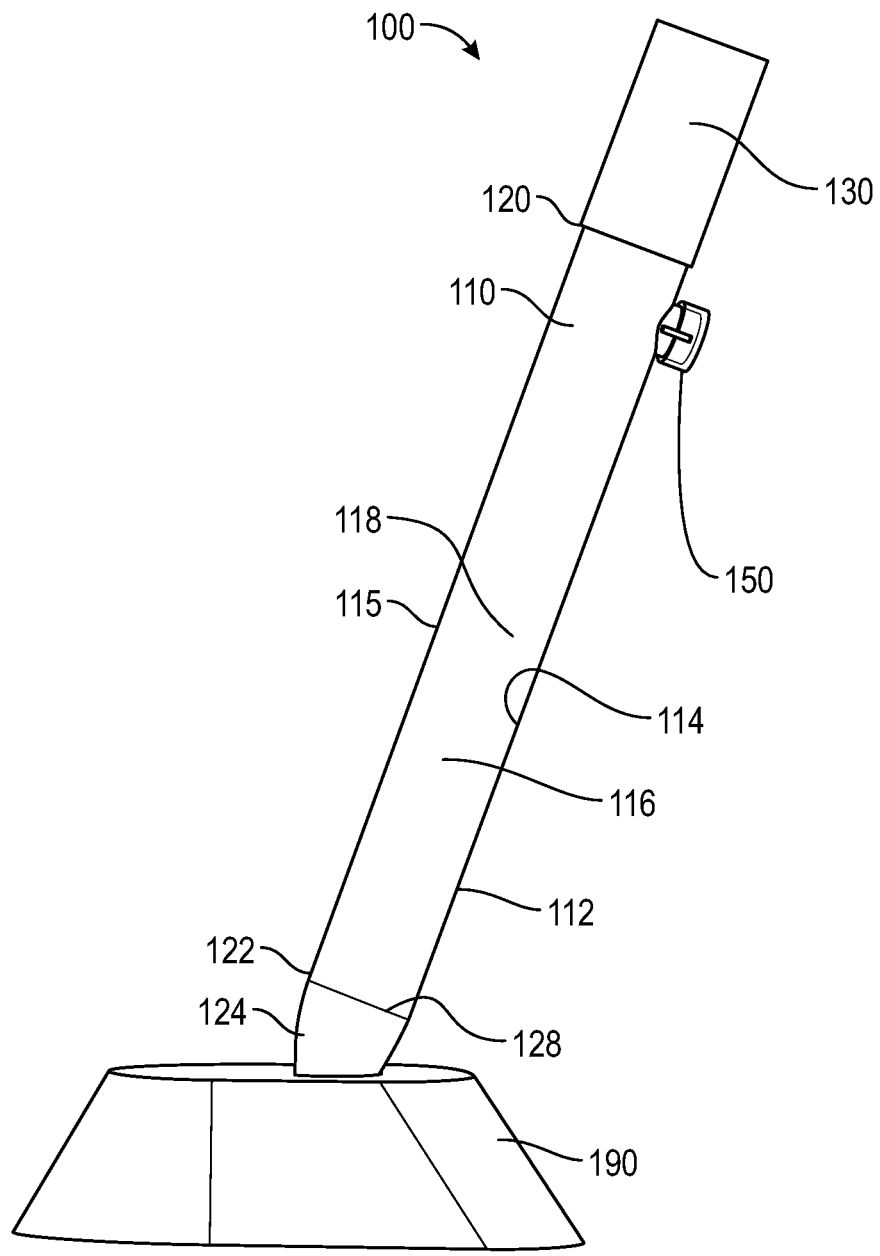
FIG. 1 illustrates a perspective view of a fluid applicator in accordance with one or more embodiments of the first aspect of present disclosure.

Before describing several exemplary embodiments of the disclosure, it is to be understood that the disclosure is not limited to the details of construction or process steps set forth in the following description. The disclosure is capable of other embodiments and of being practiced or being carried out in various ways.

For purposes of the description hereinafter, the terms "proximal", "distal", "longitudinal", and derivatives thereof shall relate to the disclosure as it is oriented in the drawing figures. However, it is to be understood that the disclosure may assume alternative variations and step sequences, except where expressly specified to the contrary. It is also to be understood that the specific devices and processes illustrated in the attached drawings, and described in the following specification, are simply exemplary embodiments of the disclosure. Hence, specific dimensions and other physical characteristics related to the embodiments disclosed herein are not to be considered as limiting.

As used herein, the use of "a," "an," and "the" includes the singular and plural.

As would be readily appreciated by skilled artisans in the relevant art, while descriptive terms such as "wall", "proximal", "side", "distal" and others are used throughout this specification to facilitate understanding, it is not intended to limit any components that can be used in combinations or individually to implement various aspects of the embodiments of the present disclosure.

As used herein, the term "microorganism" refers to a microbe or organism that is unicellular or lives in a colony of cellular organisms. Microorganisms are very diverse; they include, but are not limited to bacteria, fungi, archaea, and protozoans.

As used herein, the term "sterilization" refers to a wide variety of techniques employed to attenuate, kill or eliminate harmful or infectious agents.

Embodiments of the present disclosure are directed to a fluid applicator with precise volume dispensing control for dispensing fluids such as a disinfectant and antimicrobial agent in a controlled manner. The fluid applicator of the embodiments described in the present disclosure utilizes a one-way valve embedded within a housing having an applicator sponge. The one-way valve and applicator sponge ensures a controlled flow of fluid to the applicator sponge that is configured to uniformly distribute the disinfectant and antimicrobial agent.

FIG. 1 illustrates an perspective view of a fluid applicator 100 in accordance with one or more embodiments. As shown in FIG. 1, a first aspect of the present disclosure relates to a fluid applicator 100 having a hollow barrel 110 including a sidewall 112 having an inside surface 114 defining a chamber 116 for retaining a disinfectant or antimicrobial agent 118, an outside surface 115, an open proximal end 120, a distal end 122 including an elongate tip 124 extending distally therefrom having a passageway 126 therethrough in fluid communication with said chamber 116 and an outlet 128 on the distal end 122 of the barrel 110. In one or more embodiments, the barrel 110 is pre-filled with disinfectant or antimicrobial agent 118 prior to packaging.

An end press 130 is disposed on the open proximal end 120 to fluidly seal the open proximal end 120 of the barrel. In one or more embodiments, the end press is contoured to accommodate the end or finger of the user. In one or more embodiments, the end press 130 is deformable. In one or more embodiments, the end press is configured as a liquid medicine dropper. In one or more embodiments, the end press may be made of elastomeric material, e.g. thermoset rubber, thermoplastic vulcanizate, or thermoplastic elastomers, natural rubber, synthetic rubber, thermoplastic materials, or other easily disposable and/or recyclable material and combinations thereof. Thermoplastic elastomers include, but are not limited to, polypropylene, polyethylene and the like. Materials should be chosen to be compatible with the solution, medicament and manufacturing process being used.

Figure 2:
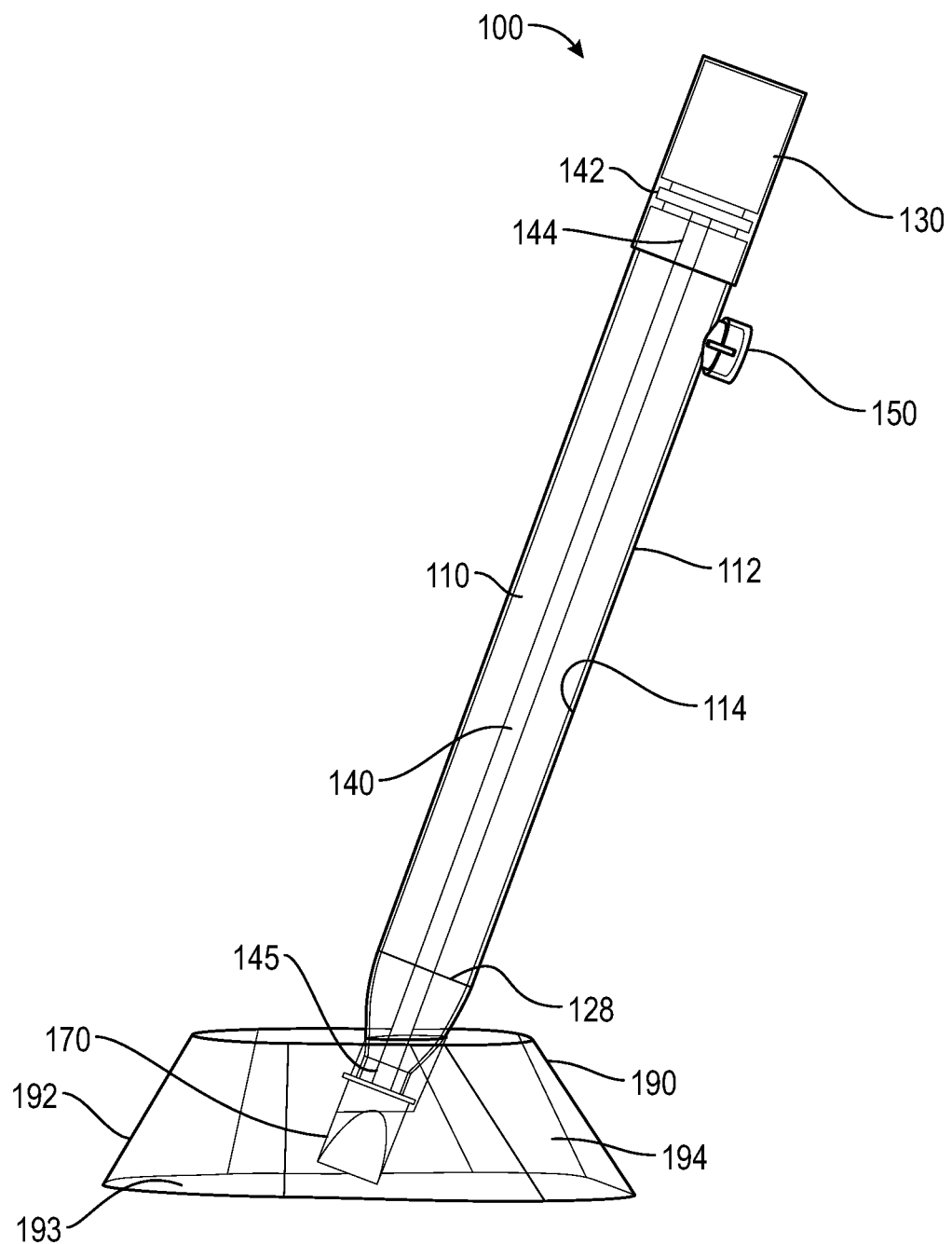
FIG. 2 illustrates a cross-sectional view of a fluid applicator in accordance with one or more embodiments of the first aspect of present disclosure.

As shown in FIG. 2, a push rod 140 is disposed within the chamber of the barrel. The push rod has a push button 142 disposed on a proximal end 144 of the push rod adjacent to the end press 130 and a piercing tip 146 disposed on a distal end 145 of the push rod. In one or more embodiments, the end press 130 is attached internally to the push rod 140. The top surface of the end press 130 is configured to provide a surface onto which distal pressure can be applied to at least partially advance the push rod into the hollow barrel 110. The end press 130 and push button 142 mechanism can be configured as a hard stop, limiting the advancement of the push rod 140 into the barrel 110. The push rod 140 movably positioned within the hollow barrel 110. The push rod is a long, slender rod that is adjacent to or attached to the push button 142 such that when the user manually depresses the end press 130, the push button 142 attached to the push rod 140 transfers linear motion from the push button to the push rod to advance the push rod in a distal direction towards a one-way valve 170. The push rod 140 has a proximal end 144 and a distal end 145, the distal end 145 has a piercing tip 146 and the proximal end 144 has a push button 142 which may be activated by depressing the end press 130. As the user continues to advances the end press 130 and push button 142 toward the distal end, the piercing tip 146 of the push rod 140 makes contact with and subsequently opens the one-way valve 170 to release disinfectant fluid into a sponge 194 as discussed below.

Figure 3:
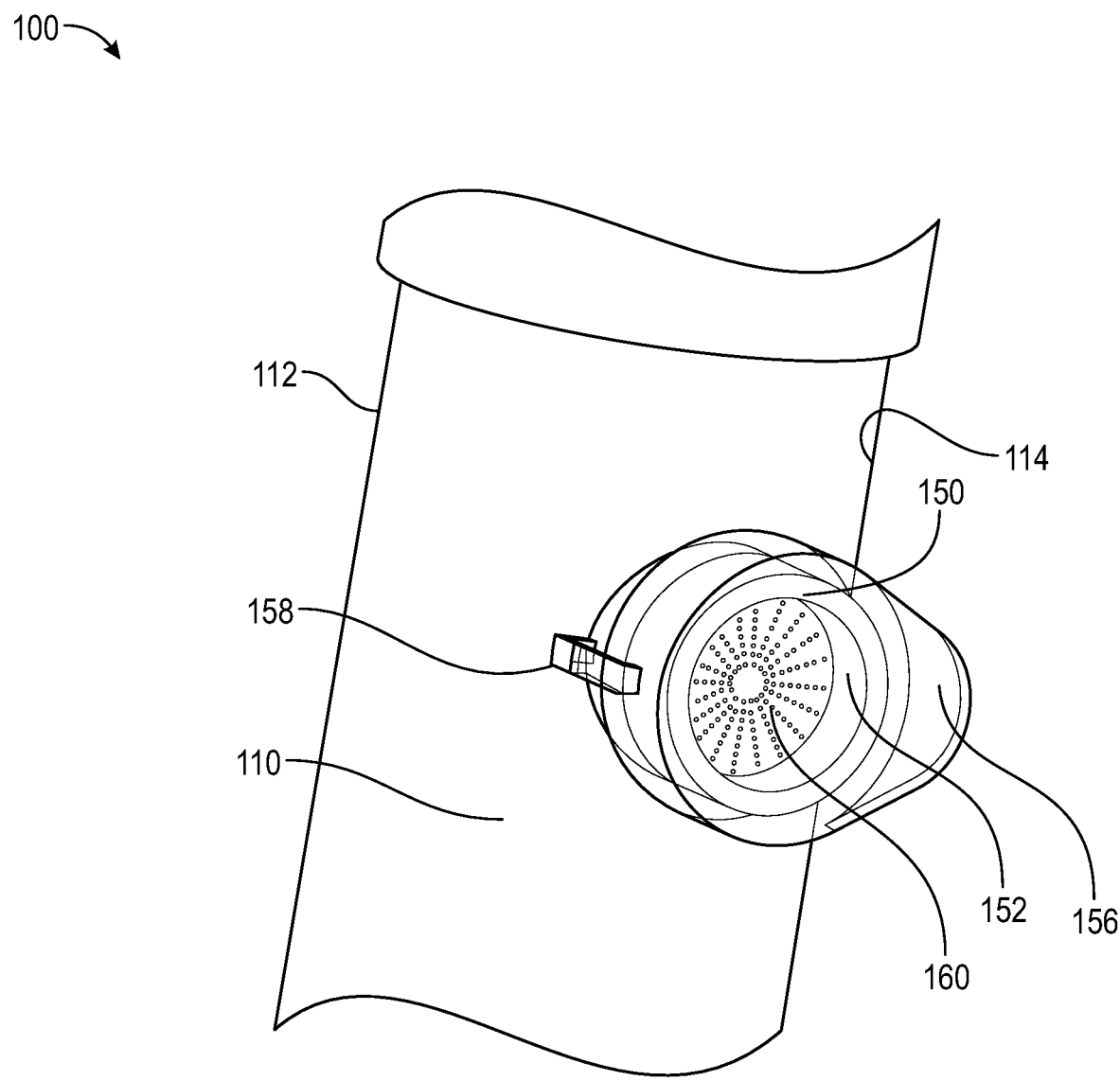
FIG. 3 illustrates an exploded view of a fluid applicator having a port, hydrophobic filter and cap in accordance with one or more embodiments of the present disclosure.

As shown in FIG. 3, a port 150 is mounted on the sidewall 112 of the barrel. In one or more embodiments, the port 150 is configured as a collar and includes at least one side wall having an inside surface defining a compartment 152.

Figure 5:
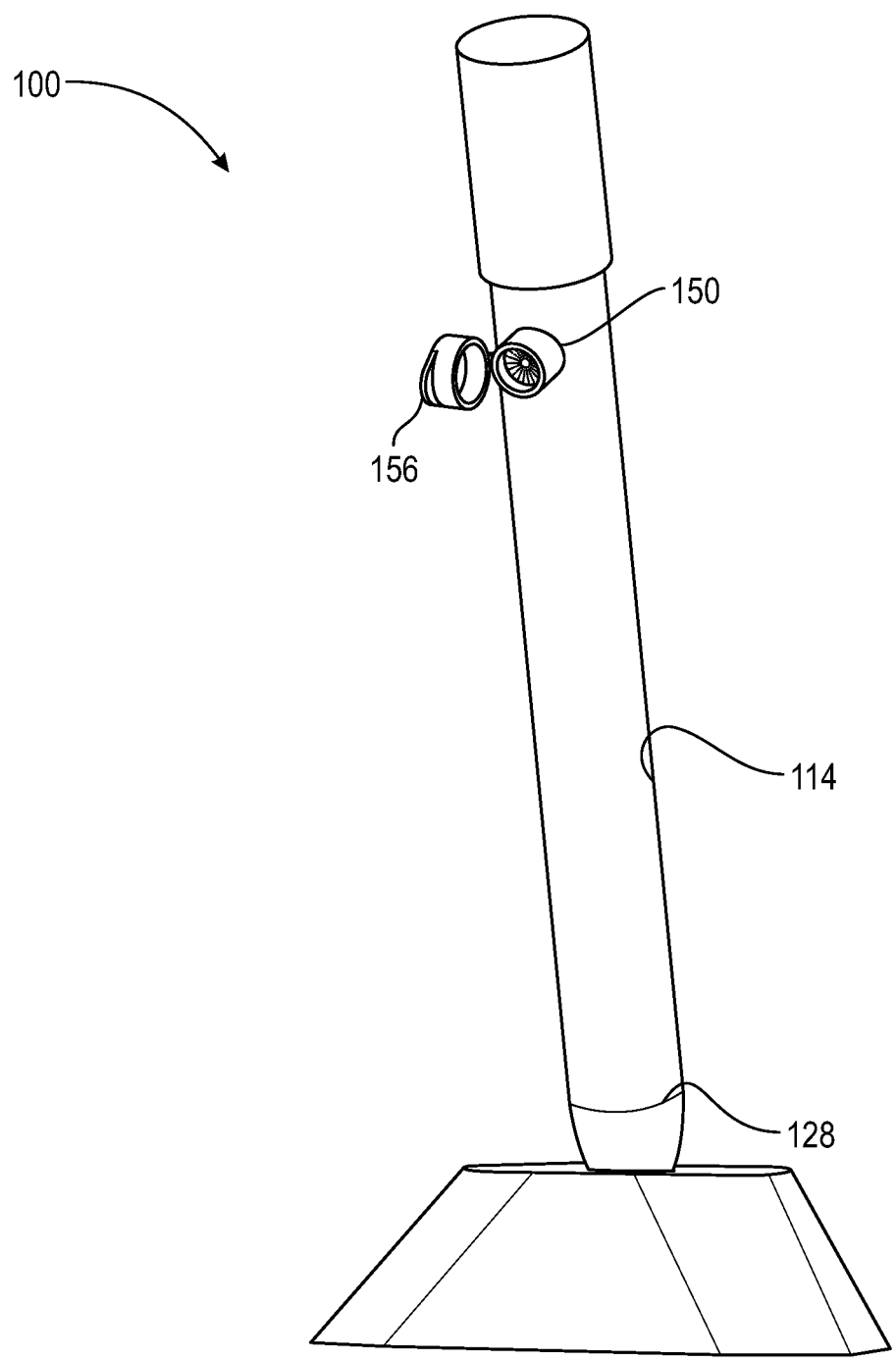
FIG. 5 illustrates a perspective view of a fluid applicator having a port, hydrophobic filter and cap in accordance with one or more embodiments of the present disclosure.

A cap 156 is attached to the port 150 via a hinge 158. In one or more embodiments, the hinge 158 opens between a fully closed position to a fully open position of at least 120 degrees as shown in FIG. 5. In one or more embodiments, the hinge is a living hinge.

A hydrophobic filter 160 is attached to the sidewall of the chamber for removing one or more air bubbles from the chamber 116. In one or more embodiments, the hydrophobic filter 160 is disposed within the port 150 on the sidewall of the chamber 116, the hydrophobic filter being in fluid communication with the chamber. In one or more embodiments, the compartment 152 of the port surrounds the hydrophobic filter 160.

The hydrophobic filter 160 removes one or more air bubbles from the chamber 116 when cap 156 is in an open position. The hydrophobic filter membrane creates a vent in the device to allow disinfectant to flow out quickly when required by the clinician upon activation via the end press as described below. Cap 156 covers the hydrophobic filter. In one or more embodiments, a cap 156 is attached to a port 150 protruding from the sidewall 112 of the barrel 110 via a hinge 158. The port and hydrophobic filter 160 and being in fluid communication with chamber 116. FIG. 3 illustrates a partial perspective view of a fluid application 100 with a hinge 158 connecting the port 150 and cap 156 in accordance with one or more embodiments of the present disclosure. In one or more embodiments, the hinge 158 is a living hinge. In one or more embodiments, cap 156 is a flip open cap. In one or more embodiments, cap 156 includes a side wall defining a longitudinal opening and a top wall between the side walls defining a recess having an interior surface. The cap 156 is capable of pivoting from an open position wherein the hydrophobic filter 160 is exposed and a closed protecting position wherein the hydrophobic filter 160 is enclosed within the longitudinal opening of the cap 156. In one or more embodiments, the port 150 and the cap 156 are molded together with the barrel 110. In an alternate embodiment, the port 150 and the barrel 110 are molded together and the cap 156 gets attached to the assembly. The hinge 158 functions such that once the hinge 158 is opened, it remains in place. In one or more embodiments, the hinge 158 may have a butterfly shape with a central section that serves as a hinge and the two wings on the sides to make it snap into place. Prior to use, the cap 156 is in an initial closed position until the cap 156 is opened prior to use. In one or more embodiments, the hinge 158 opens between a fully closed position to a fully open position to the required degree of at least 120 degrees. In one or more embodiments, the cap 156 is both easy to open by flipping it backwards (the end of the user moving away from the hydrophobic filter) and the cap 156 is also sufficiently tight to provide minimum sterility assurance levels.

Figure 4:
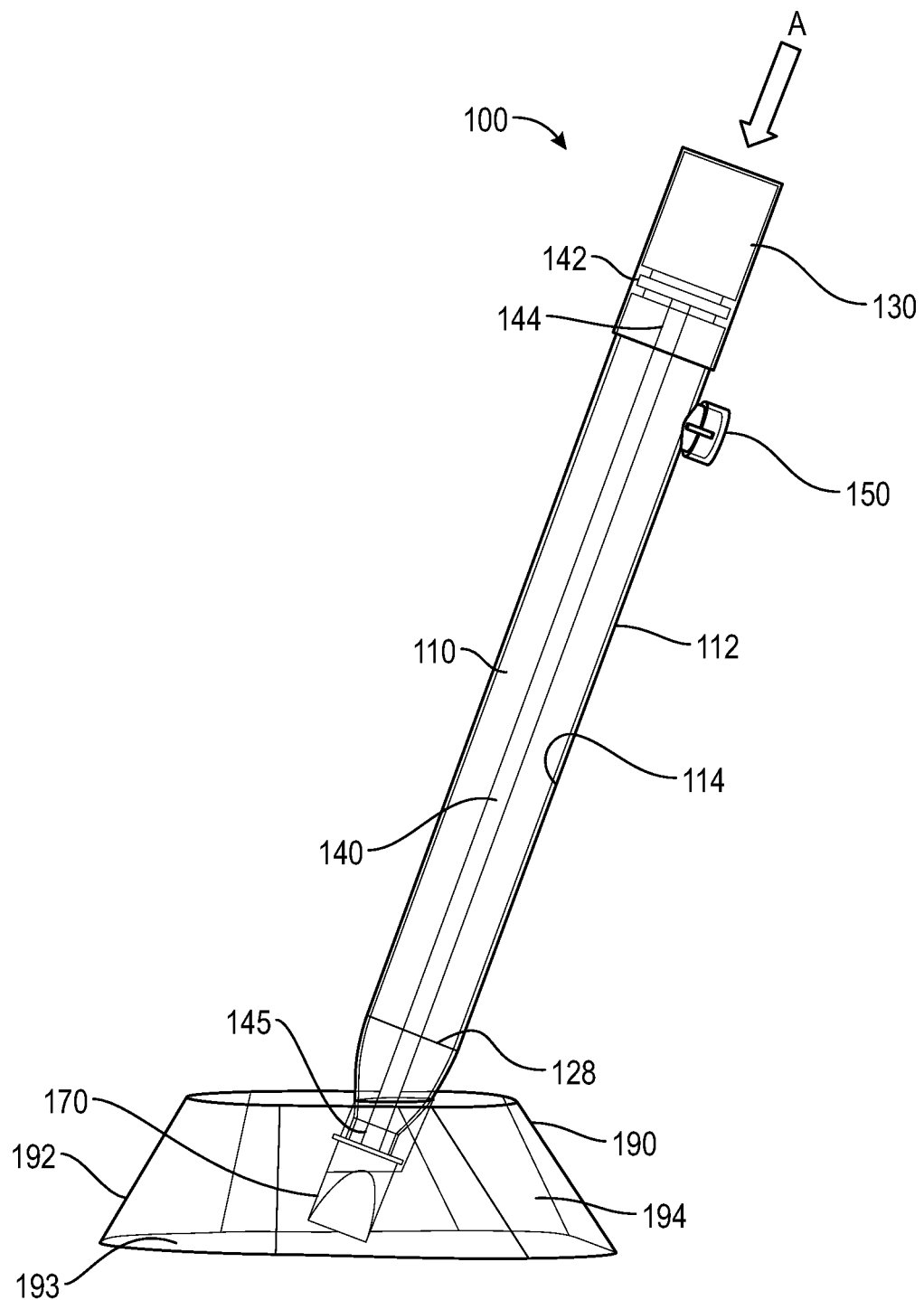
FIG. 4 illustrates a cross-sectional view of a fluid applicator depicting direction "A" in accordance with one or more embodiments of the first aspect of present disclosure.
Figure 6:
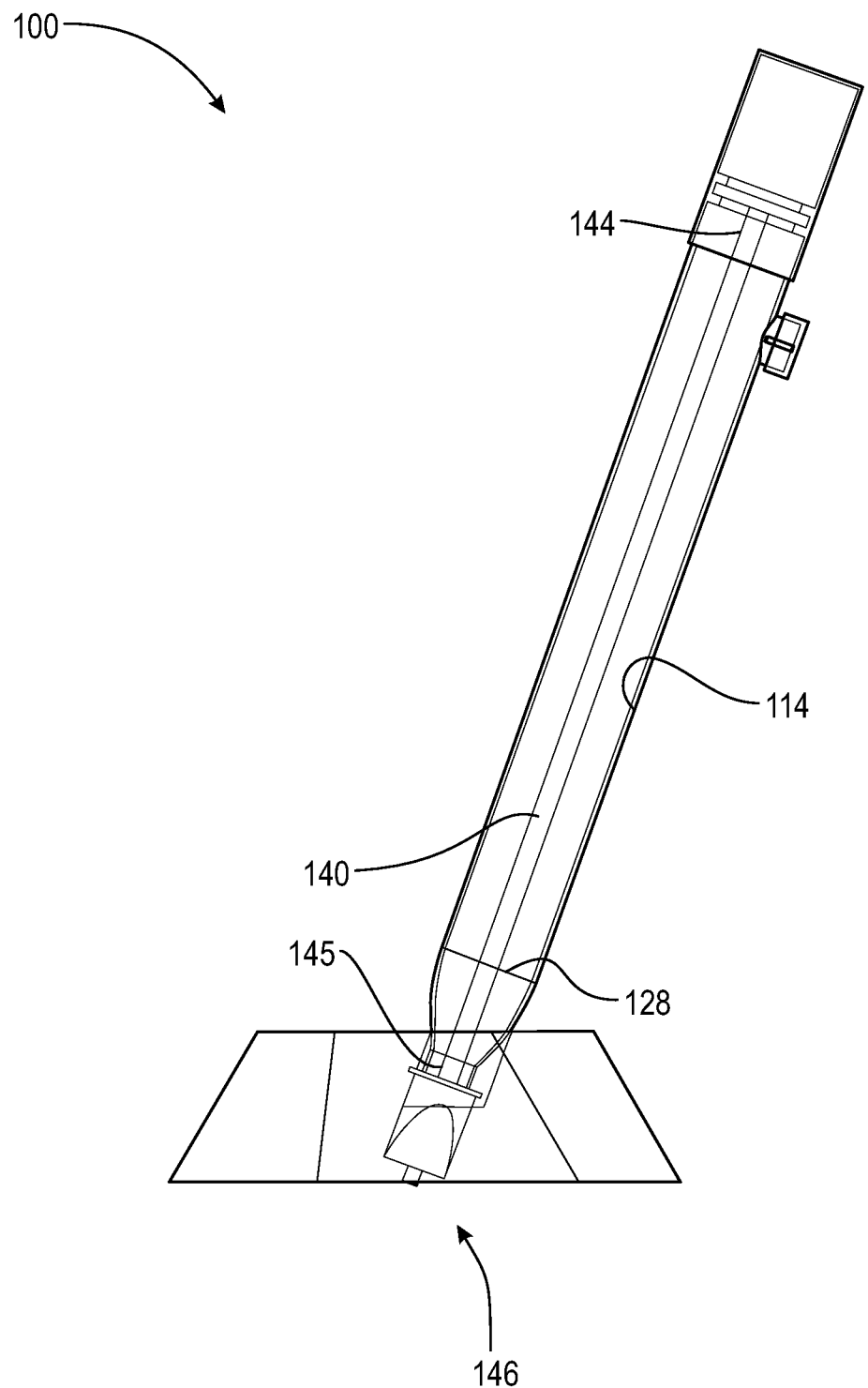
FIG. 6 illustrates a cross-sectional view of a fluid applicator with a piercing tip of the push rod penetrating a one-way valve in accordance with one or more embodiments of the first aspect of present disclosure.

As shown in FIG. 4, one-way valve 170 is disposed on the outlet on the distal end of the barrel. The one-way valve may be a duckbill valve, an umbrella valve, a ball-check valve, diaphragm check valve, swing check valve, stop-check valve, lift-check valve or a combination thereof. In one or more embodiments, the one-way valve is a duckbill valve. In one or more embodiments, the one-way valve 170 is disposed between the distal tip of the chamber and sponge 194. In some embodiments, as shown in FIGS. 2 through 8, the one-way valve 170 is configured to seal the distal end of the chamber 116 to prevent disinfectant from leaking or flowing out of the chamber 116 during packaging and prior to use of the fluid applicator 100, the chamber 116 being in fluid communication with the hollow barrel 110. The one-way valve is in fluid communication with the chamber 116 of the hollow barrel 110, and the one-way valve permits fluid evacuation from the chamber 116 of the hollow barrel 110 but prevents air or fluid intake into the chamber 116 when the end press 130 is manually depressed and released. The one-way valve may be a duckbill valve, an umbrella valve, a ball-check valve, diaphragm check valve, swing check valve, stop-check valve, lift-check valve or a combination thereof. In one or more preferred embodiments, the one-way valve is a duckbill valve. The one-way valve 170 is composed of elastomeric components that act as backflow prevention devices or one-way valves or check valves. In one or more embodiments, the one-way valve 170 has elastomeric lips in the shape of a duckbill which prevent backflow and allow forward flow. The one-way valve 170 is configured to break or release disinfectant from the outlet 128 on the distal end 122 of the barrel 110 having a passageway 126 therethrough in fluid communication with the chamber 116 when the end press 130 is pushed in a distal direction thereby advancing the push button toward the distal end upon sufficient application of hydraulic force due to advancement of the push rod 140 distally into the hollow barrel 110. In one or more embodiments, as shown in FIG. 6, the distal tip of the push rod is configured to pierce the one-way valve to release and direct fluid out of the barrel 110. The one-way valve is assembled into a sponge 194 which gets wet when disinfectant flows into it after activation of the device as will be discussed further below. The one-way valve 170 is configured to uniformly distribute fluid from the passageway 126 to the sponge 194.

A disinfectant 118 is disposed within the chamber between the one-way valve and the end press. In one or more embodiments, the disinfectant or antimicrobial agent is selected from the group consisting essentially of isopropyl alcohol, ethanol, 2-propanol, butanol, methylparaben, ethylparaben, propylparaben, propyl gallate, butylated hydroxyanisole (BHA), butylated hydroxytoluene, t-butylhydroquinone, chloroxylenol, chlorhexidine, chlorhexidine diacetate, chlorhexidine gluconate, povidone iodine, alcohol, dichlorobenzyl alcohol, dehydroacetic acid, hexetidine, triclosan, hydrogen peroxide, colloidal silver, benzethonium chloride, benzalkonium chloride, octenidine, antibiotic, and mixtures thereof. In one or more embodiments, the fluid applicator 100 is a single use pre-filled delivery device. A single use sterile delivery device of the present disclosure reduces the risk associated with contamination due to manual filling.

Figure 7:
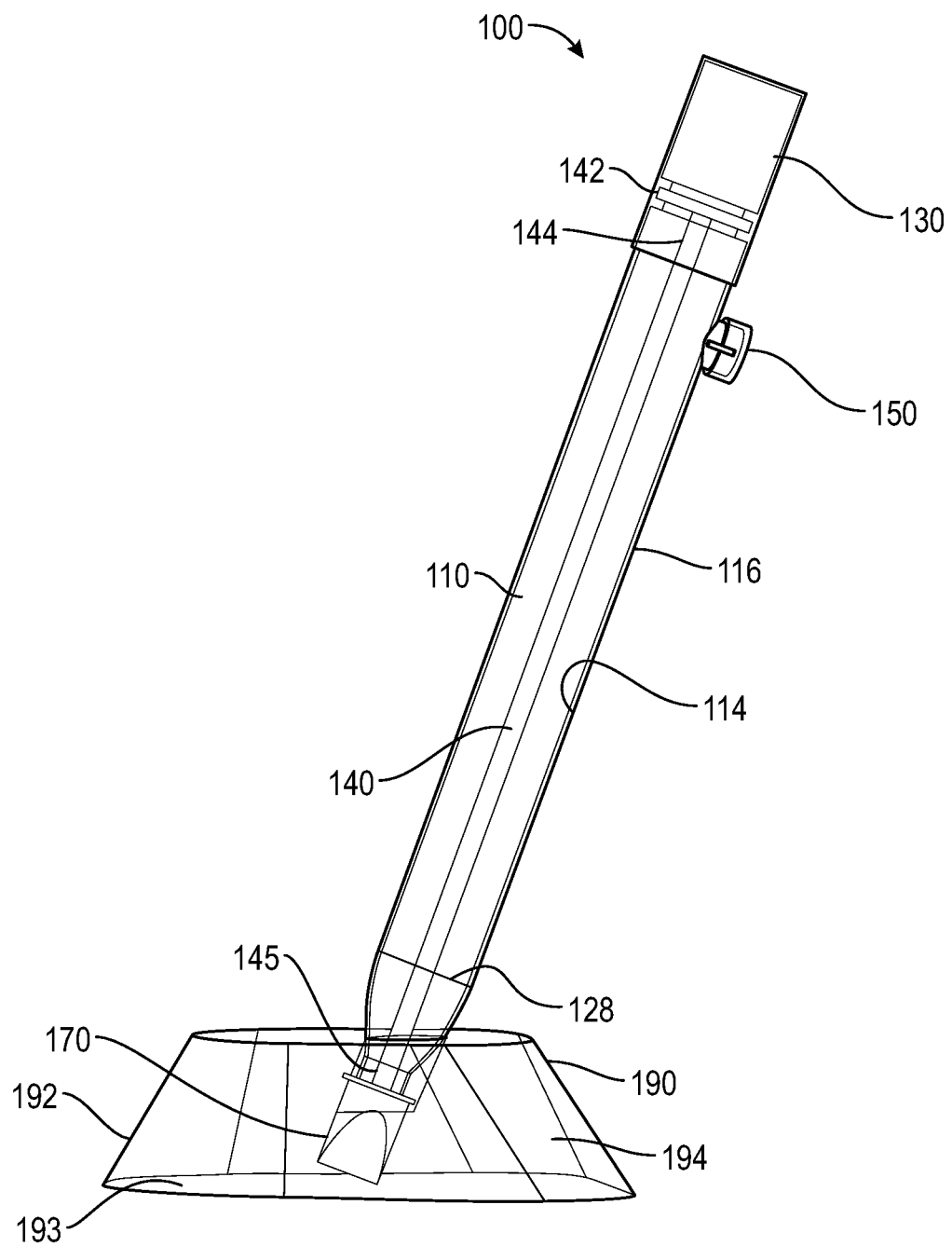
FIG. 7 illustrates a cross-sectional view of a fluid applicator in accordance with one or more embodiments of the first aspect of present disclosure.

As shown in FIG. 7, a housing 190 having a base 192 and an open proximal end 193 is at the distal end of the barrel and a sponge 194 is disposed or affixed in the base 192 of the housing 190. In some embodiments, the sponge 194 is removably affixed to the base 192. In some embodiments, the sponge 194 is removably affixed by a non-permanent medical grade adhesive or hook-and-loop. In some embodiments, the sponge 194 is non removably affixed to the base 192 by a permanent medical grade adhesive. At least a portion of the sponge 194 is in fluid communication with the chamber 116 that retains a disinfectant or antimicrobial agent 118 such that the disinfectant or antimicrobial agent 118 will flow from the chamber 116 via the one-way valve 170 to permeate though and across the sponge 194. In one or more embodiments, the barrel 110 is at an angle relative to the housing 190. In some embodiments, the base 192 is perpendicular to the barrel 110. In some embodiments, the base 192 is at an angle relative to the barrel 110. The base 192 can be angled to ergonomically assist in the application of fluid by the sponge 194.

As shown in FIG. 7, the one-way valve 170 partially extends into the base 192 of the housing 190 and is embedded into the fluid applicator sponge 194. In one or more embodiments, the tip and the one-way valve are positioned a distance from the open proximal end of the housing. The one-way valve is at least partially embedded into the housing 190 and provides a controlled and constant flow of fluid.

In one or more embodiments, the fluid applicator sponge 194 is configured to uniformly distribute disinfectant released from the one-way valve 170. In one or more embodiments, the fluid applicator sponge 194 is made of an absorbent material. In one or more embodiments, the absorbent material is a nonwoven material, foam or a sponge. In a specific embodiment, the foam is a polyurethane foam.

The hydrophobic filter may be either molded or assembled in the body of the barrel 110. A chamber 116 containing both air and liquid may be positioned such that the air is located in the region of the distal end 122 of barrel 110 and the liquid is positioned away from the outlet. The hydrophobic filter may be positioned away from the distal end 122 of barrel 110, such that when activated, the hydrophobic filter preferentially expels air over liquid. The hydrophobic filter does not allow disinfectant to flow through it but allows for air pressure equalization so that disinfectant 118 can flow rapidly to the sponge 194. Due to the combination of the one-way valve 170 and hydrophobic filter 160, a steady flow of disinfectant is provided by the fluid applicator 100 of the present disclosure without requiring a flow distribution sponge to dampen or limit rapid and uncontrolled gushing of fluid upon breakage of an ampoule. Thus, an advantage of the present disclosure over prior art is that the passageway of the chamber 116 and the one-way valve 170 can be adjacent to the sponge 194 without the need of a flow distribution sponge, or more generally a tortuous paths or absorbent materials for the purposes of limiting or slowing of gushing or rapid flow. In particular, common applicators having a breakable ampoule or more generally a single-release or uncontrolled release device implement flow limiting materials before the applicator sponge to dampen the rapid flow.

The barrel 110, push rod 140, port 150, cap 156 or housing 190 can be made from a rigid material including any of a number of types of plastic materials such as polycarbonate, polypropylene, polyethylene, glycol-modified polyethylene terephthalate, acrylonitrile butadiene styrene or any other moldable plastic material used in medical devices. In one or more specific embodiments, the barrel 110, push rod 140, port 150, cap 156 or housing 190 can be made from of a rigid material, including but not limited to polymers such as a polypropylene or polyethylene material. In one or more embodiments, the cap and the locking lid comprises a polypropylene or polyethylene material.

In one or more embodiments, the barrel, port, push rod, push button or cap are made of a polypropylene or polyethylene material.

In one or more embodiments, the fluid applicator 100 of the present disclosure includes volume scale markings 180 on an outer surface 115 of the barrel 110.

Figure 8A:
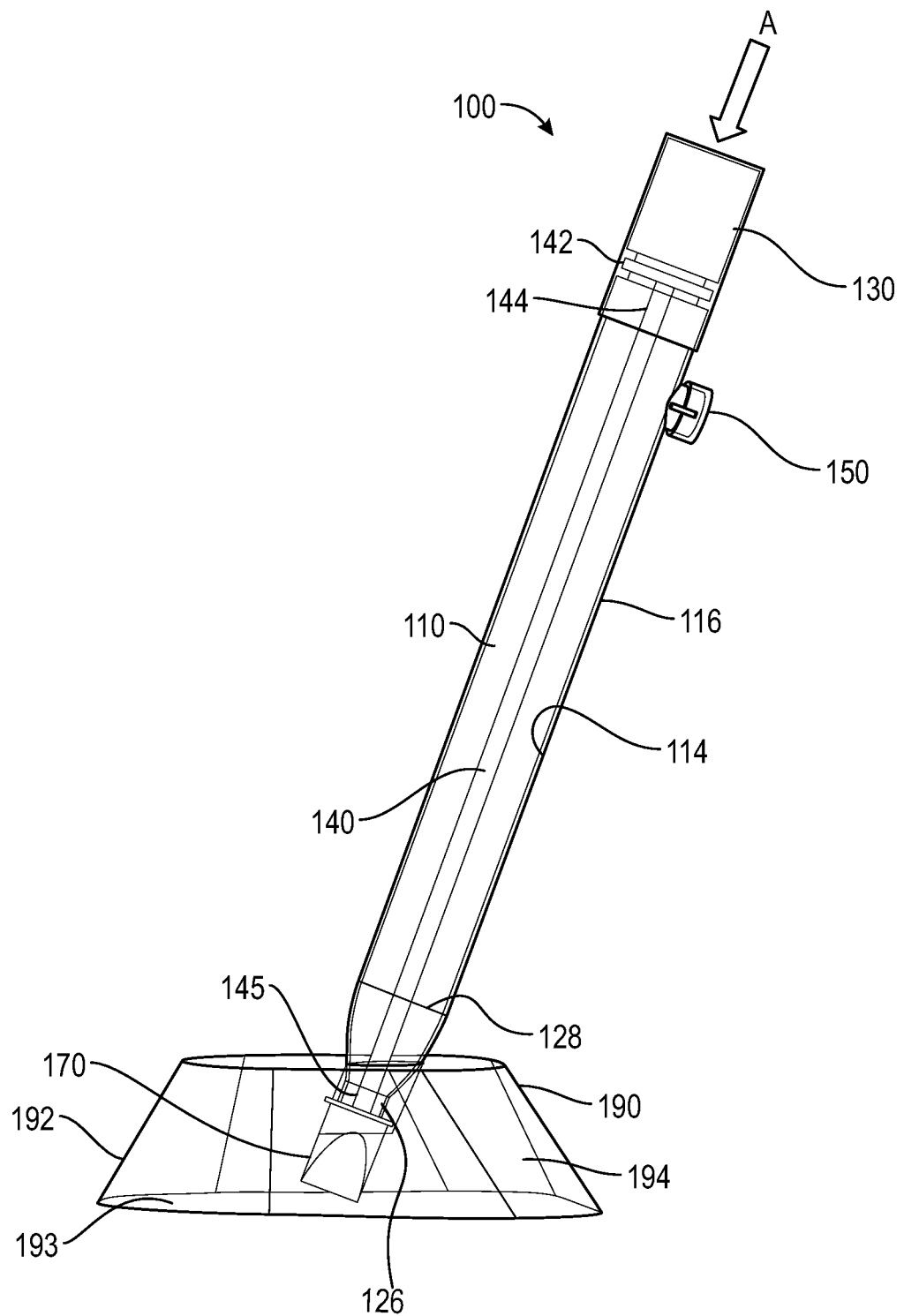
FIGS. 8A-8D illustrate a fluid applicator in accordance with one or more embodiments of the first aspect of present disclosure in use.
Figure 8B:
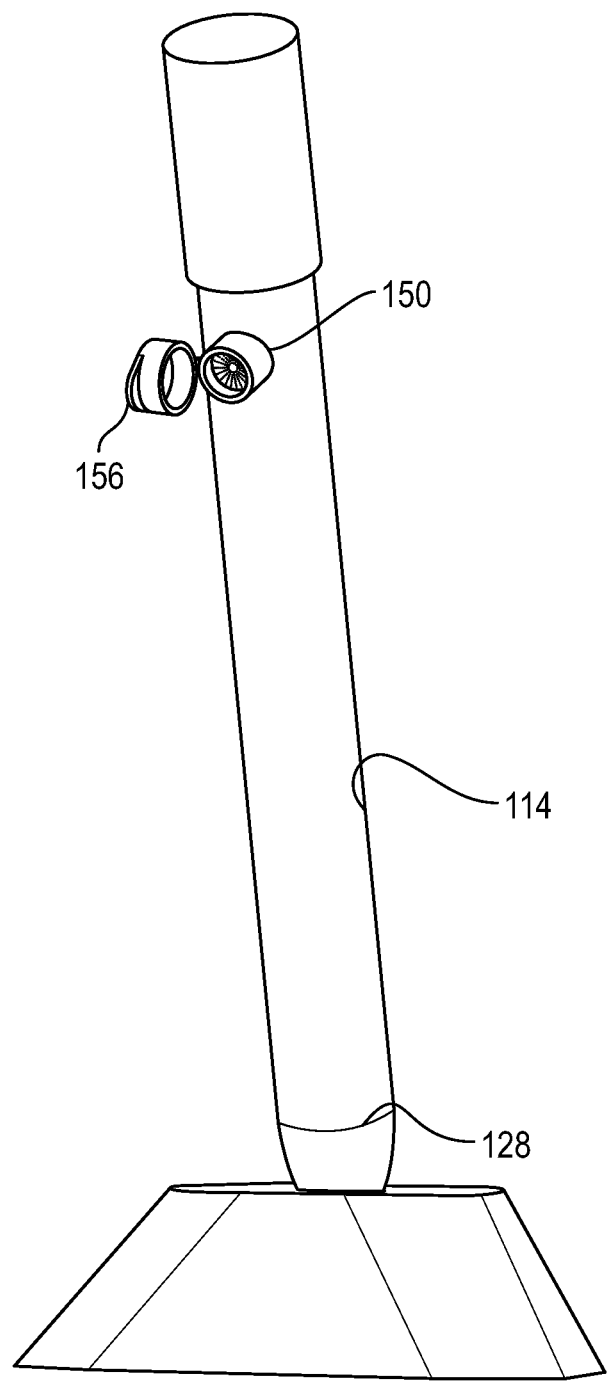
Figure 8C:
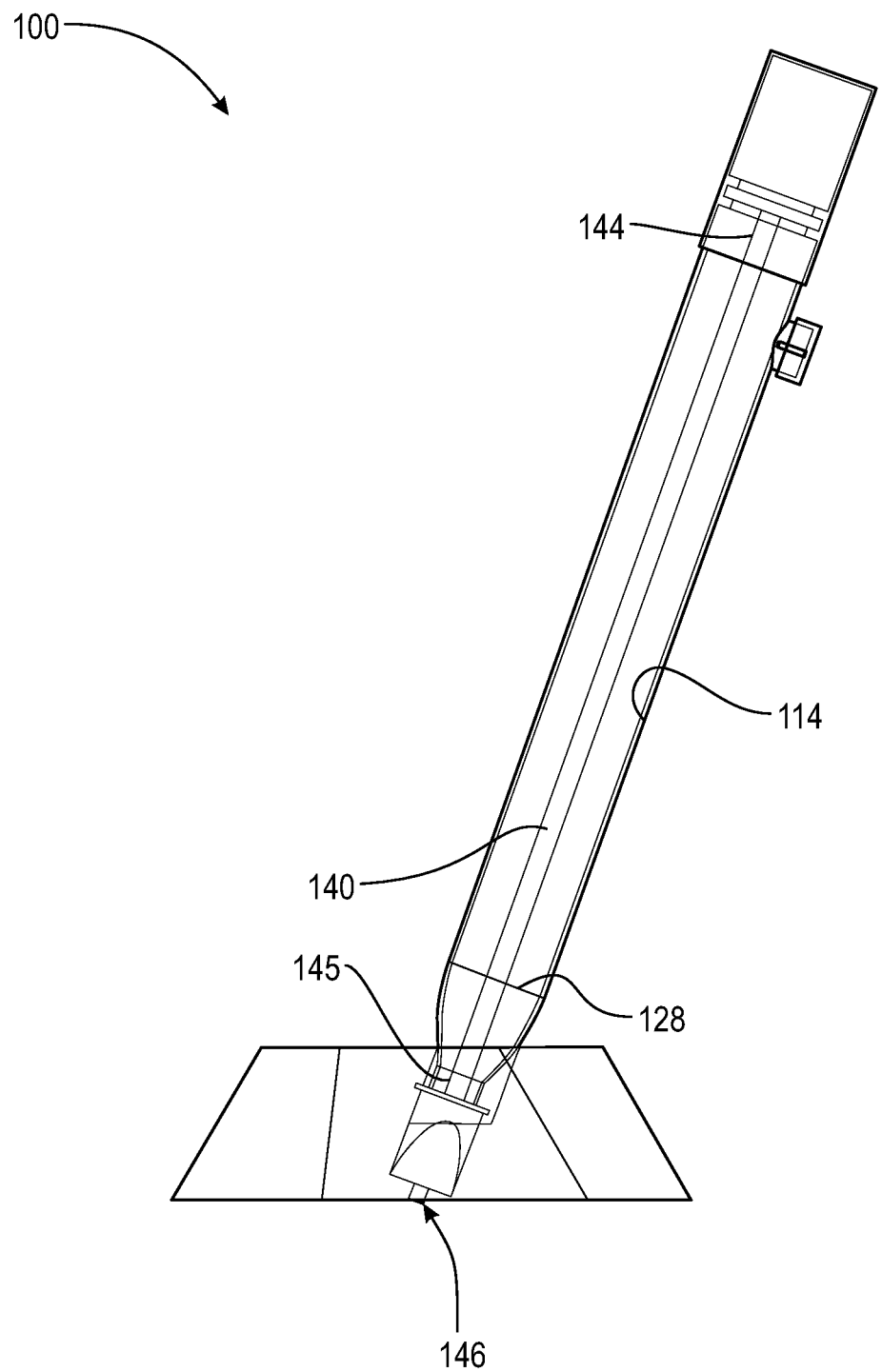
Figure 8D:
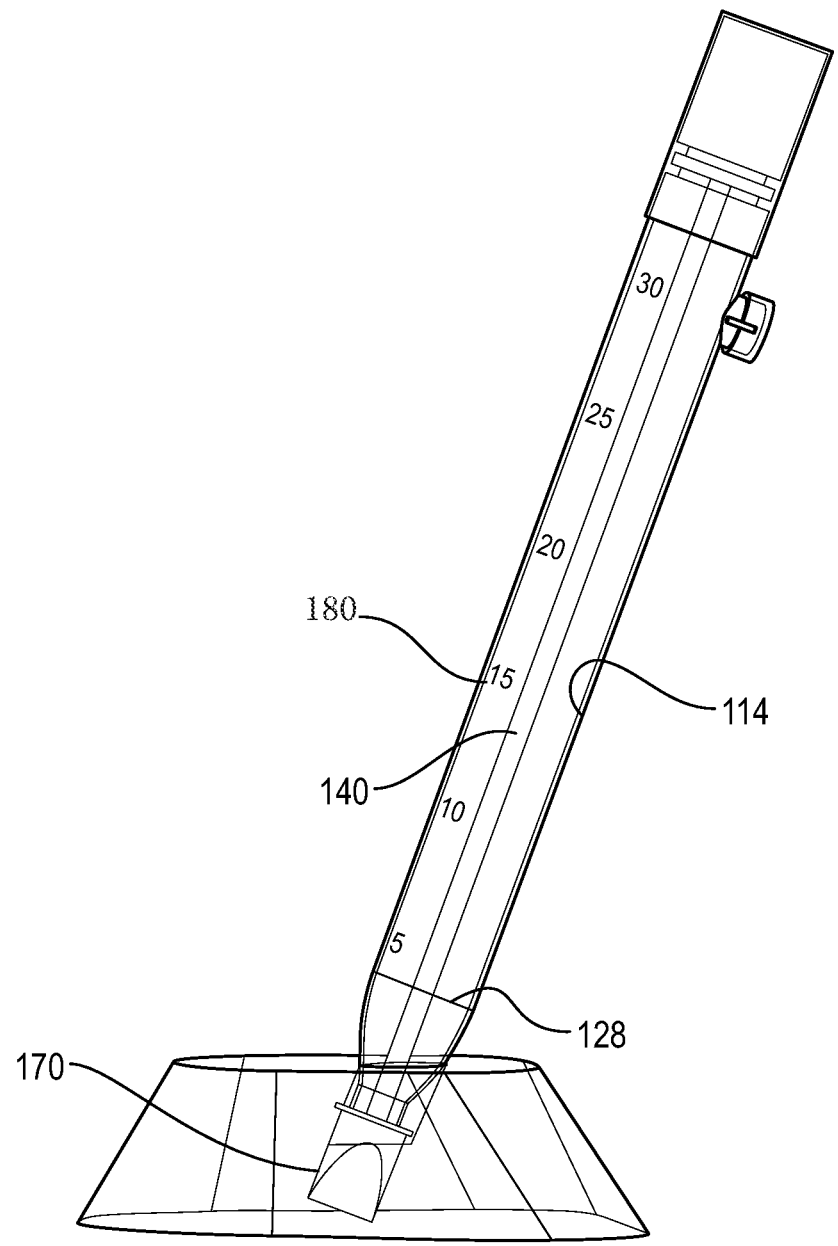
Figure 9:
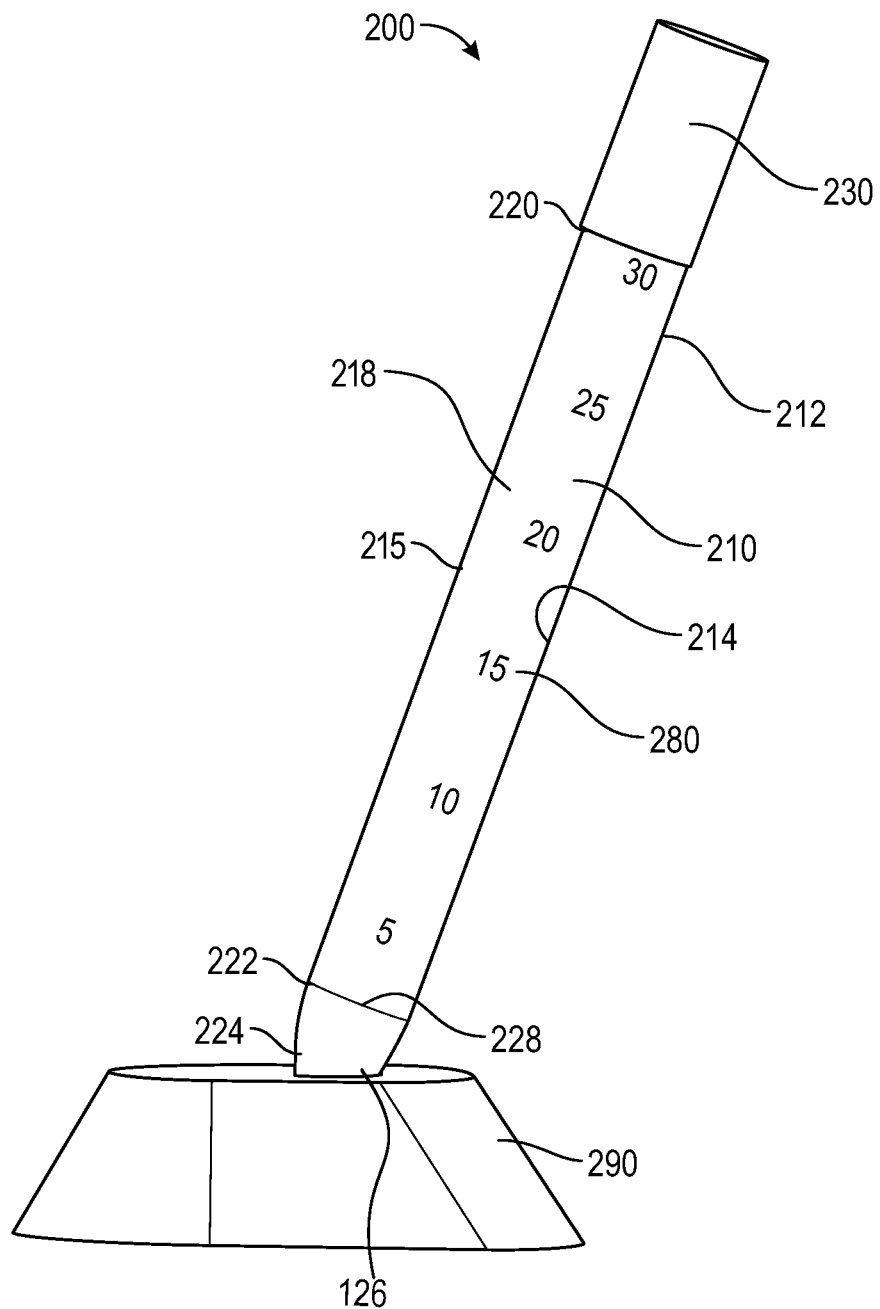
FIG. 9 illustrates a perspective view of a fluid applicator in accordance with one or more embodiments of the second aspect of present disclosure.

As shown in FIG. 8A, in operation once the fluid applicator 100 is taken out of primary packaging, the clinician depresses the end press 130 with sufficient force to advance the end press 130 and the push button 142 in a distal direction "A". As shown in FIG. 8B, the cap 156 on the port 150 is flipped open. The hydrophobic filter 160 disposed within the port 150 now allows exchange of air but disinfectant 118 cannot flow across the membrane of hydrophobic filter 160 due to hydrophobic nature. As shown in FIG. 8C, upon application of continued depression of the end press 130, the push rod 140 advances toward the one-way valve 170 such that the piercing tip 146 of the push rod 140 pierces open the one-way valve 170 to allow disinfectant 118 to flow out from the chamber 116 in a controlled and constant matter onto the fluid applicator sponge 194. In one or more embodiments, the end press 130 is now pressed similar to a cam or thrust device to push the push rod 140 into the one-way valve 170 to rupture or open the one-way valve 170 creating a passage for the disinfectant 118 to flow into the sponge 194 which gets soaked with fluid disinfectant 118. When the cap 156 is in an open position, the hydrophobic filter 160 provides for a vented chamber which can allow disinfectant 118 to flow into the sponge 194 upon activation using pressure equalization with external environment achieved by venting. The quick flow of disinfectant out of the chamber is achieved by equalizing pressure with the external atmosphere using the hydrophobic membrane. The hydrophobic filter 160 contained within the port 150 allows all of the disinfectant to flow into the sponge upon activation. The clinician can control the volume and flow rate of the disinfectant dispensed by further pressing the end press 130 to continue to release fluid or releasing the end press to cause the push rod 140 to retract such that the piercing tip 146 withdraws from the one-way valve 170 to seal and close the one-way valve 170 to stop further disinfectant 118 from being released onto the fluid applicator sponge 194 as shown in FIG. 8D. The fluid applicator 100 can now be used for skin preparation and disinfection.

A second aspect of present disclosure relates to a fluid applicator 200 having an additional advantage of controlling volume and flow rate of disinfectant flow into a disinfection sponge. As shown in FIGS. 9-14 fluid applicator 200 of the second aspect of present disclosure has a hollow barrel 210 including a sidewall 212 having an inside surface 214 defining a chamber 216 for retaining a disinfectant or antimicrobial agent 218, an outside surface 215, an open proximal end 220, a distal end 222 including an elongate tip 224 extending distally therefrom having a passageway 226 therethrough in fluid communication with said chamber 216 and an outlet 228 on the distal end 222 of the barrel 210. In one or more embodiments, the barrel 210 is pre-filled with disinfectant or antimicrobial agent 218 prior to packaging. A plurality of volume scale markings 280 are disposed on an outer surface of the barrel to ensure that a correct dosage is metered by the clinician.

An end press 230 is disposed on the open proximal end 220 to fluidly seal the open proximal end 220 of the barrel. In one or more embodiments, the end press is contoured to accommodate the end or finger of the user. In one or more embodiments, the end press 230 is deformable. In one or more embodiments, the end press is configured as a liquid medicine dropper. In one or more embodiments, the end press may be made of elastomeric material, e.g. thermoset rubber, thermoplastic vulcanizate, or thermoplastic elastomers, natural rubber, synthetic rubber, thermoplastic materials, or other easily disposable and/or recyclable material and combinations thereof. Thermoplastic elastomers include, but are not limited to, polypropylene, polyethylene and the like. Materials should be chosen to be compatible with the solution, medicament and manufacturing process being used.

Figure 10:
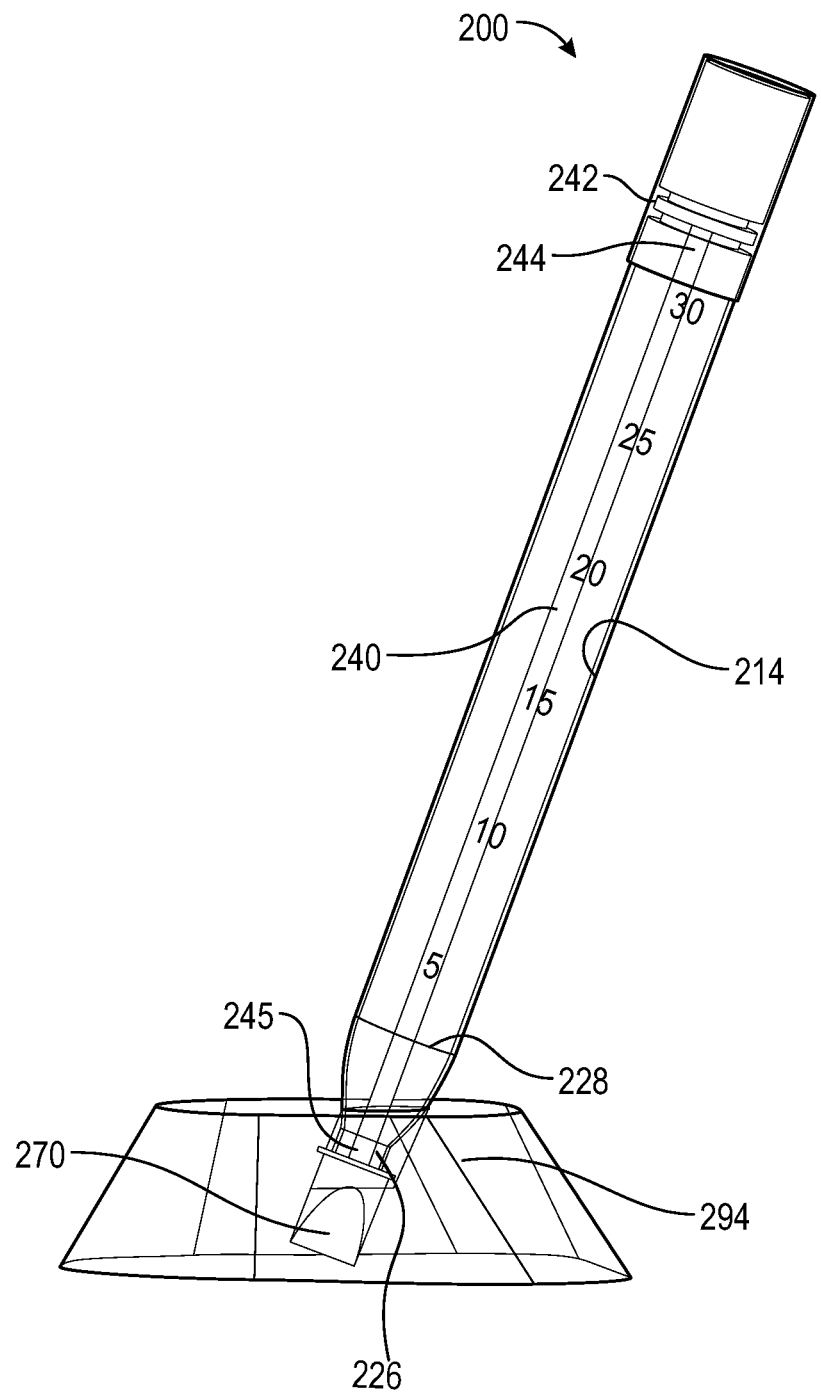
FIG. 10 illustrates a cross-sectional view of a fluid applicator in accordance with one or more embodiments of the second aspect of present disclosure.
Figure 11:
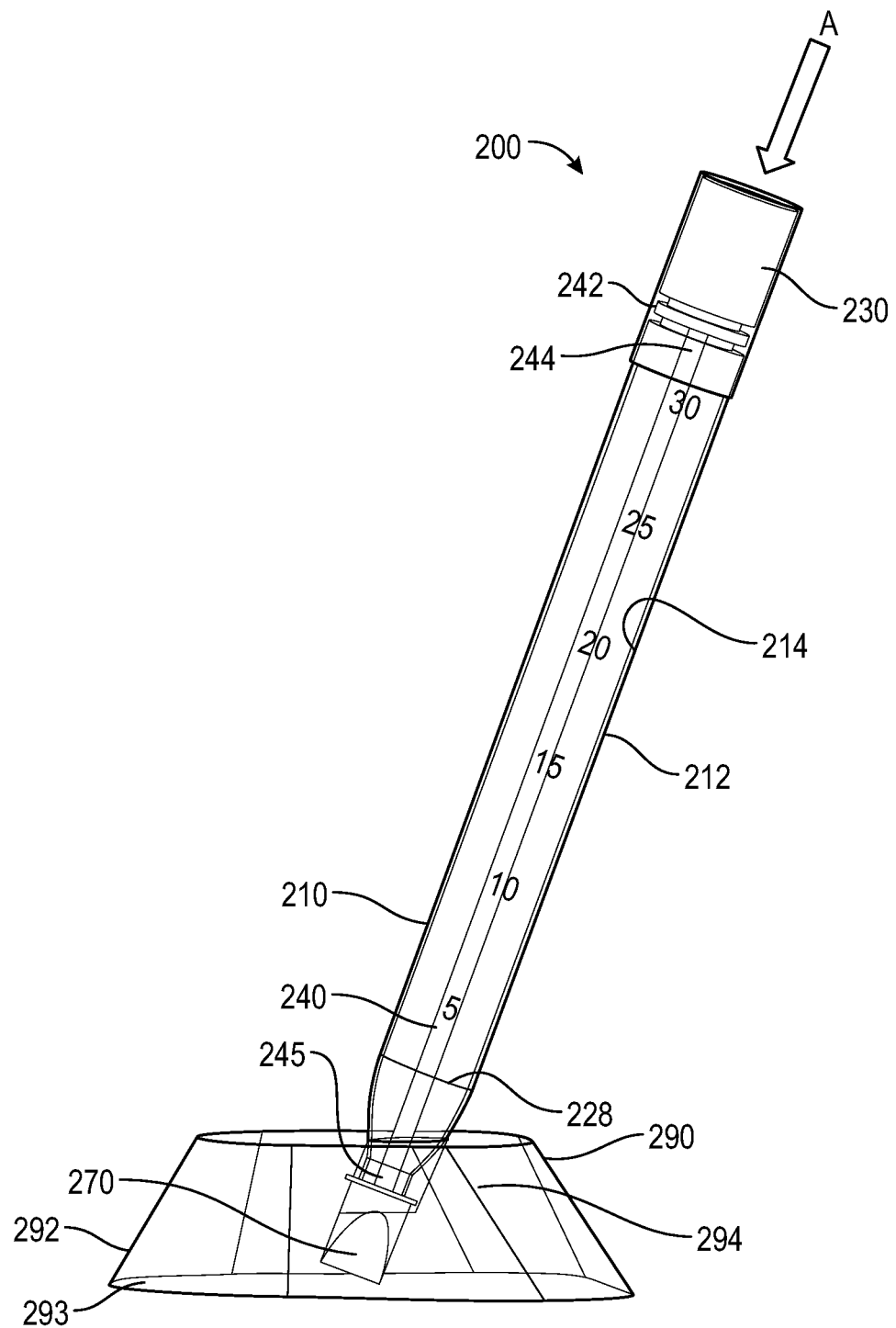
FIG. 11 illustrates a cross-sectional view of a fluid applicator depicting direction "A" in accordance with one or more embodiments of the second aspect of present disclosure.
Figure 12:
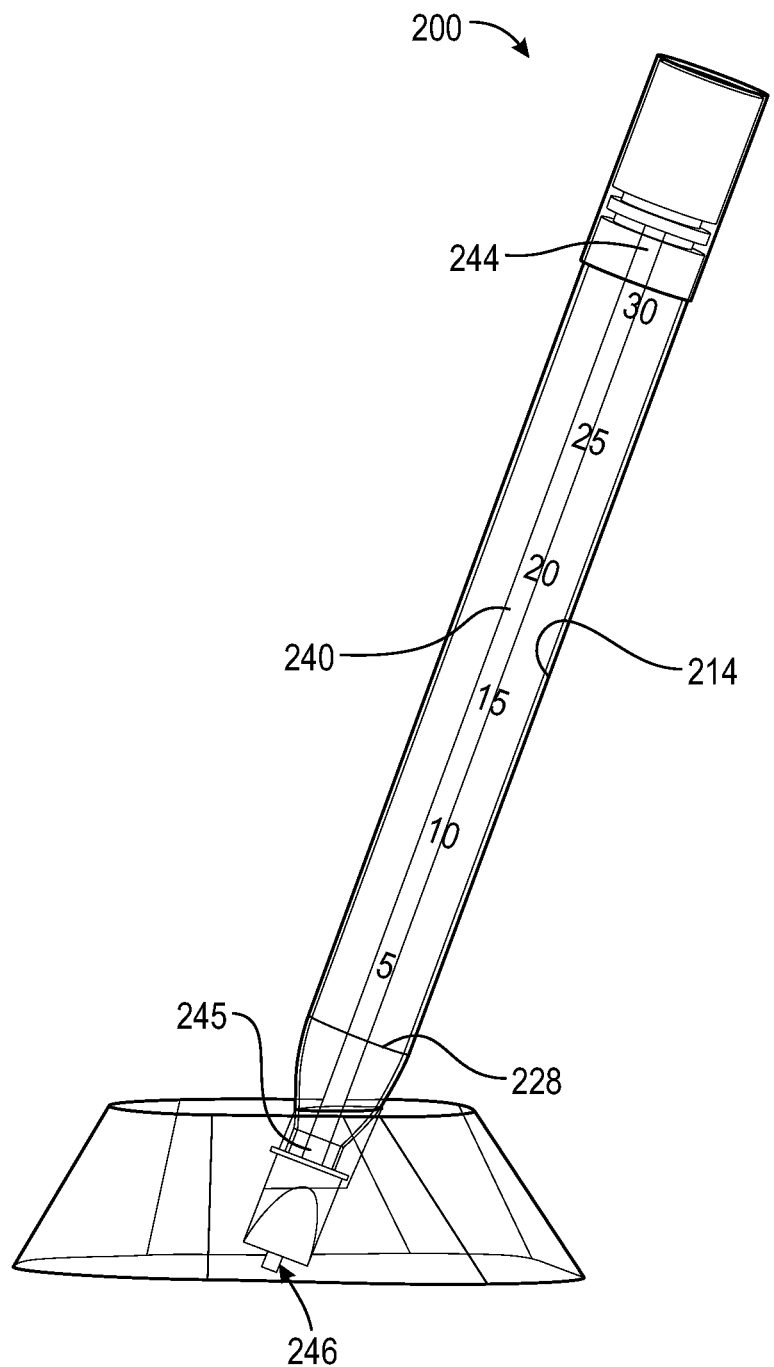
FIG. 12 illustrates a cross-sectional view of a fluid applicator with a piercing tip of the push rod penetrating a one-way valve in accordance with one or more embodiments of the second aspect of present disclosure.

As shown in FIG. 10, a push rod 240 is disposed within the chamber of the barrel. The push rod has a push button 242 disposed on a proximal end 244 of the push rod adjacent to the end press 230 and a piercing tip 246 disposed on a distal end 245 of the push rod. In one or more embodiments, the end press 230 is attached internally to the push rod 240. The top surface of the end press 230 is configured to provide a surface onto which distal pressure can be applied to at least partially advance the push rod into the hollow barrel 210. The end press 230 and push button 242 mechanism can be configured as a hard stop, limiting the advancement of the push rod 240 into the barrel 210. As shown in FIG. 11, the push rod 240 movably positioned within the hollow barrel 210 in direction "A". The push rod is a long, slender rod that is adjacent to or attached to the push button 242 such that when the user manually depresses the end press 230, the push button 242 attached to the push rod 240 transfers linear motion from the push button to the push rod to advance the push rod in a distal direction towards a one-way valve 270. As shown in FIG. 12, the push rod 240 has a proximal end 244 and a distal end 245, the distal end 245 has a piercing tip 246 and the proximal end 244 has a push button 242 which may be activated by depressing the end press 230. As the user continues to advance the end press 230 and push button 242 toward the distal end, the piercing tip 246 of the push rod 240 makes contact with and subsequently opens the one-way valve 270 to release disinfectant fluid into a sponge 294 as discussed below. As the user releases the end press 230, the push rod 240 retracts and subsequently closes the one-way valve 270 to stop the flow of disinfectant fluid into a sponge 294 as discussed below.

Figure 13:
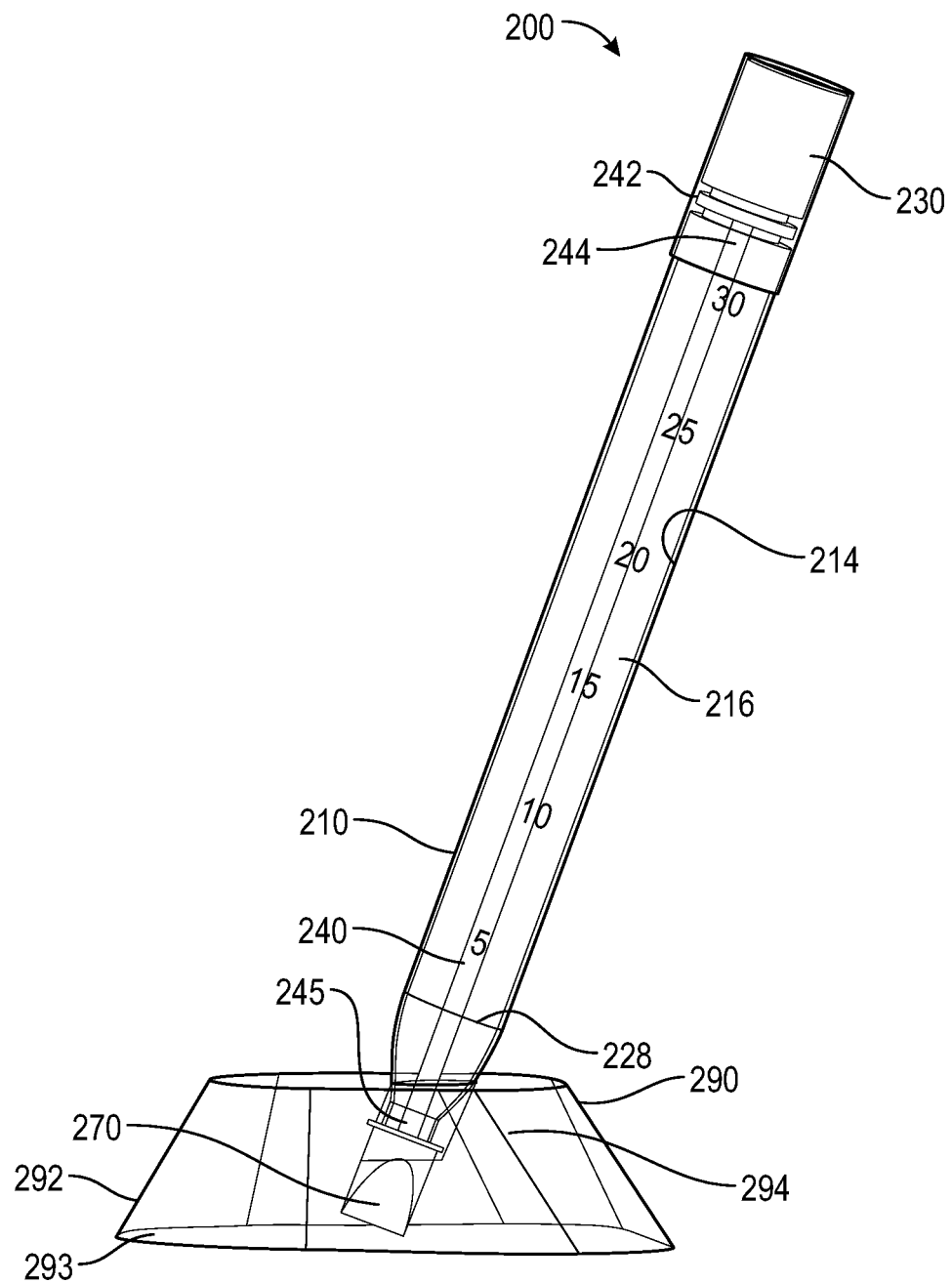
FIG. 13 illustrates a cross-sectional view of a fluid applicator in accordance with one or more embodiments of the second aspect of present disclosure.

As shown in FIG. 13, a one-way valve 270 is disposed on the outlet on the distal end of the barrel. The one-way valve may be a duckbill valve, an umbrella valve, a ball-check valve, diaphragm check valve, swing check valve, stop-check valve, lift-check valve or a combination thereof. In one or more embodiments, the one-way valve is a duckbill valve. In one or more embodiments, the one-way valve 270 is disposed between the distal tip of the chamber and sponge 294. In some embodiments, as shown in FIGS. 10-15D, the one-way valve 270 is configured to seal the distal end of the chamber 216 to prevent disinfectant from leaking or flowing out of the chamber 216 during packaging and prior to use of the fluid applicator 200, the chamber 216 being in fluid communication with the hollow barrel 210. The one-way valve is in fluid communication with the chamber 216 of the hollow barrel 210, and the one-way valve permits fluid evacuation from the chamber 216 of the hollow barrel 210 but prevents air or fluid intake into the chamber 216 when the end press 230 is manually depressed and released. The one-way valve may be a duckbill valve, an umbrella valve, a ball-check valve, diaphragm check valve, swing check valve, stop-check valve, lift-check valve or a combination thereof. In one or more preferred embodiments, the one-way valve is a duckbill valve. The one-way valve 270 is composed of elastomeric components that act as backflow prevention devices or one-way valves or check valves. In one or more embodiments, the one-way valve 270 has elastomeric lips in the shape of a duckbill which prevent backflow and allow forward flow. The one-way valve 270 is configured to break or release disinfectant from the outlet 228 on the distal end 222 of the barrel 210 having a passageway 226 therethrough in fluid communication with the chamber 216 when the end press 230 is pushed in a distal direction thereby advancing the push button toward the distal end upon sufficient application of hydraulic force due to advancement of the push rod 240 distally into the hollow barrel 210. In one or more embodiments, the distal tip of the push rod is configured to pierce the one-way valve to release and direct fluid out of the barrel 210. The one-way valve is assembled into a sponge 294 which gets wet when disinfectant flows into it after activation of the device as will be discussed further below. The one-way valve 270 is configured to uniformly distribute fluid from the passageway 226 to the sponge 294.

A disinfectant 218 is disposed within the chamber between the one-way valve and the end press. In one or more embodiments, the disinfectant or antimicrobial agent is selected from the group consisting essentially of isopropyl alcohol, ethanol, 2-propanol, butanol, methylparaben, ethylparaben, propylparaben, propyl gallate, butylated hydroxyanisole (BHA), butylated hydroxytoluene, t-butylhydroquinone, chloroxylenol, chlorohexidine, chlorhexidine diacetate, chlorohexidine gluconate, povidone iodine, alcohol, dichlorobenzyl alcohol, dehydroacetic acid, hexetidine, triclosan, hydrogen peroxide, colloidal silver, benzethonium chloride, benzalkonium chloride, octenidine, antibiotic, and mixtures thereof. In one or more embodiments, the fluid applicator 200 is a single use pre-filled delivery device. A single use sterile delivery device of the present disclosure reduces the risk associated with contamination due to manual filling.

A housing 290 having a base 292 and an open proximal end 293 is at the distal end of the barrel and a sponge 294 is disposed or affixed in the base 292 of the housing 290. In some embodiments, the sponge 294 is removably affixed to the base 292. In some embodiments, the sponge 294 is removably affixed by a non-permanent medical grade adhesive or hook-and-loop. In some embodiments, the sponge 294 is non removably affixed to the base 292 by a permanent medical grade adhesive. At least a portion of the sponge 294 is in fluid communication with the chamber 216 that retains a disinfectant or antimicrobial agent 218 such that the disinfectant or antimicrobial agent 218 will flow from the chamber 216 via the one-way valve 270 to permeate though and across the sponge 294. In one or more embodiments, the barrel 210 is at an angle relative to the housing 290. In some embodiments, the base 292 is perpendicular to the barrel 210. In some embodiments, the base 292 is at an angle relative to the barrel 210. The base 292 can be angled to ergonomically assist in the application of fluid by the sponge 294.

The one-way valve 270 partially extends into the base 292 of the housing 290 and is embedded into the fluid applicator sponge 294. In one or more embodiments, the tip and the one-way valve are positioned a distance from the open proximal end of the housing. The one-way valve is at least partially embedded into the housing 290 and provides a controlled and constant flow of fluid.

In one or more embodiments, the fluid applicator sponge 294 is configured to uniformly distribute disinfectant released from the one-way valve 270. In one or more embodiments, the fluid applicator sponge 294 is made of an absorbent material. In one or more embodiments, the absorbent material is a nonwoven material, foam or a sponge. In a specific embodiment, the foam is a polyurethane foam.

The hydrophobic filter may be either molded or assembled in the body of the barrel 210. A chamber 216 containing both air and liquid may be positioned such that the air is located in the region of the distal end 122 of barrel 210 and the liquid is positioned away from the outlet. The hydrophobic filter may be positioned away from the distal end 122 of barrel 210, such that when activated, the hydrophobic filter preferentially expels air over liquid. The hydrophobic filter does not allow disinfectant to flow through it but allows for air pressure equalization so that disinfectant 218 can flow rapidly to the sponge 294. Due to the combination of the one-way valve 270 and deformable end press 230, a steady flow of disinfectant is provided by the fluid applicator 200 of the present disclosure without requiring a flow distribution sponge to dampen or limit rapid and uncontrolled gushing of fluid upon piercing of the one-way valve. Thus, an advantage of the present disclosure over prior art is that the passageway of the chamber 216 and the one-way valve 270 can be adjacent to the sponge 294 without the need of a flow distribution sponge, or more generally a tortuous paths or absorbent materials for the purposes of limiting or slowing of gushing or rapid flow. In particular, common applicators having a breakable ampoule or more generally a single-release or uncontrolled release device implement flow limiting materials before the applicator sponge to dampen the rapid flow.

The barrel 210, push rod 240 or housing 290 can be made from any of a number of types of plastic materials such as polycarbonate, polypropylene, polyethylene, glycol-modified polyethylene terephthalate, acrylonitrile butadiene styrene or any other moldable plastic material used in medical devices. In one or more embodiments, the cap and the locking lid comprises a polypropylene or polyethylene material.

In one or more embodiments, the barrel, port, push rod, push button or cap are made of a polypropylene or polyethylene material.

In one or more embodiments, the fluid applicator 200 of the present disclosure includes volume scale markings 280 on an outer surface 215 of the barrel 210.

Figure 14:
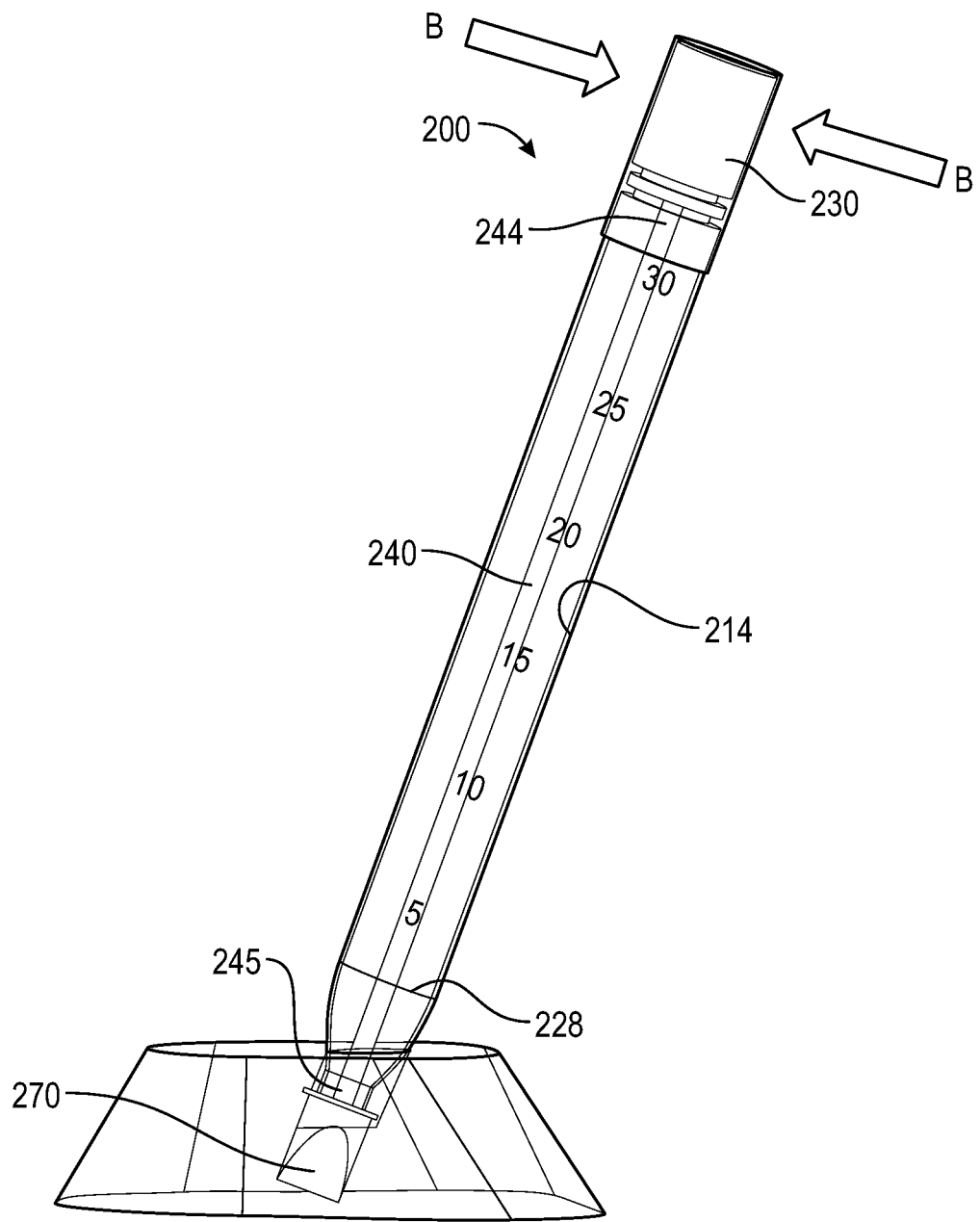
FIG. 14 illustrates a cross-sectional view of a fluid applicator depicting direction "B" in accordance with one or more embodiments of the second aspect of present disclosure.
Figure 15A:
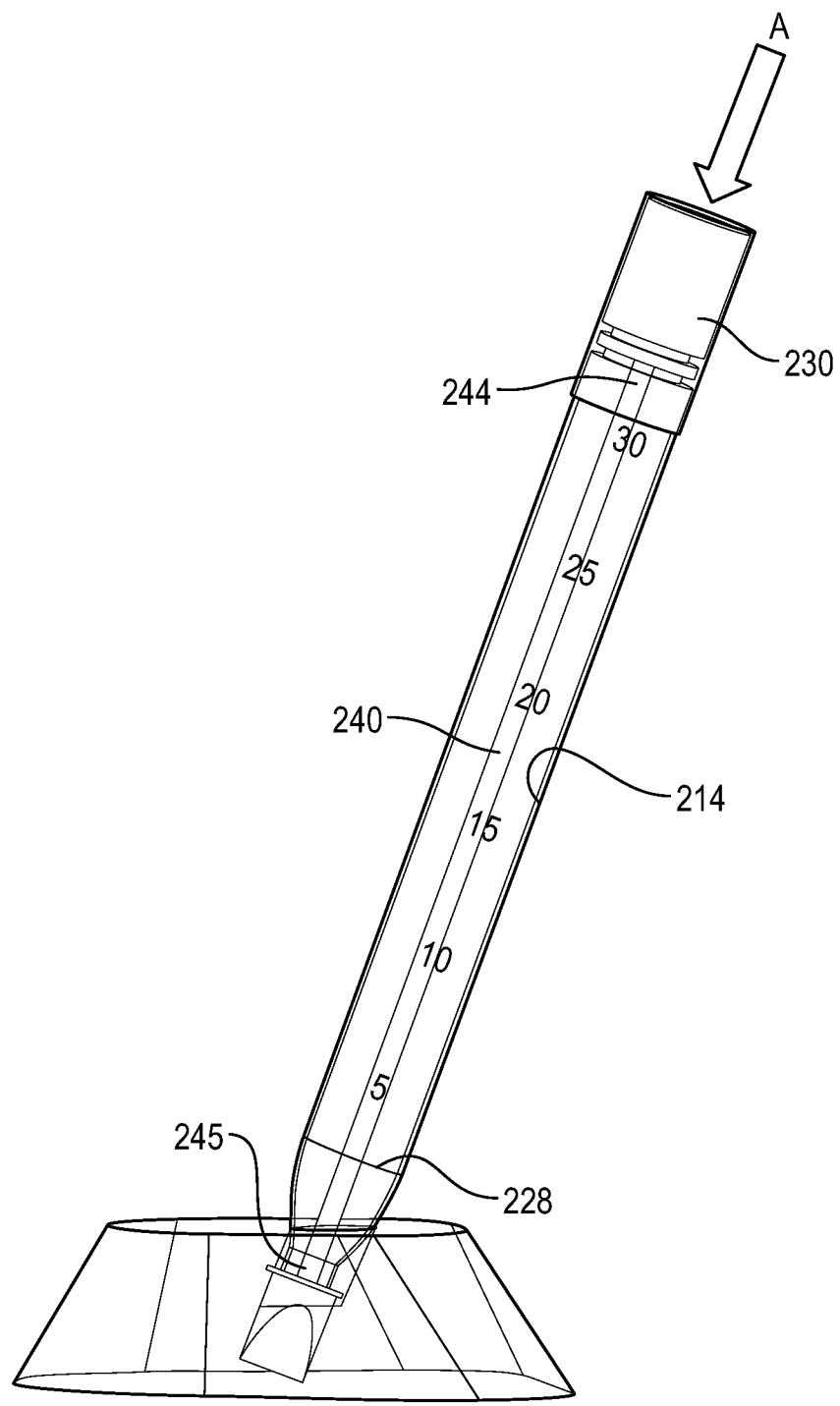
FIG. 15A-15D illustrate a fluid applicator in accordance with one or more embodiments of the second aspect of present disclosure in use.
Figure 15B:
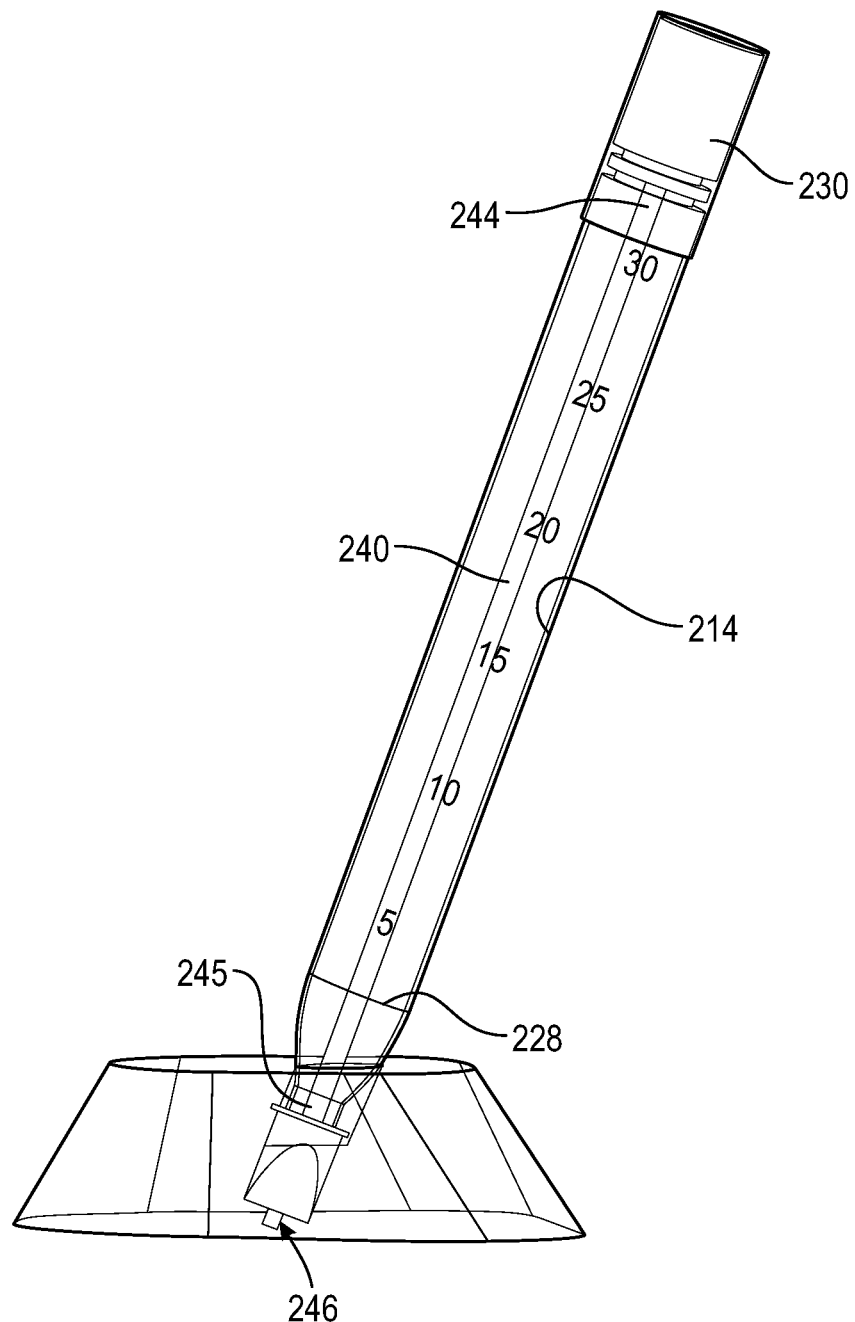
Figure 15C:
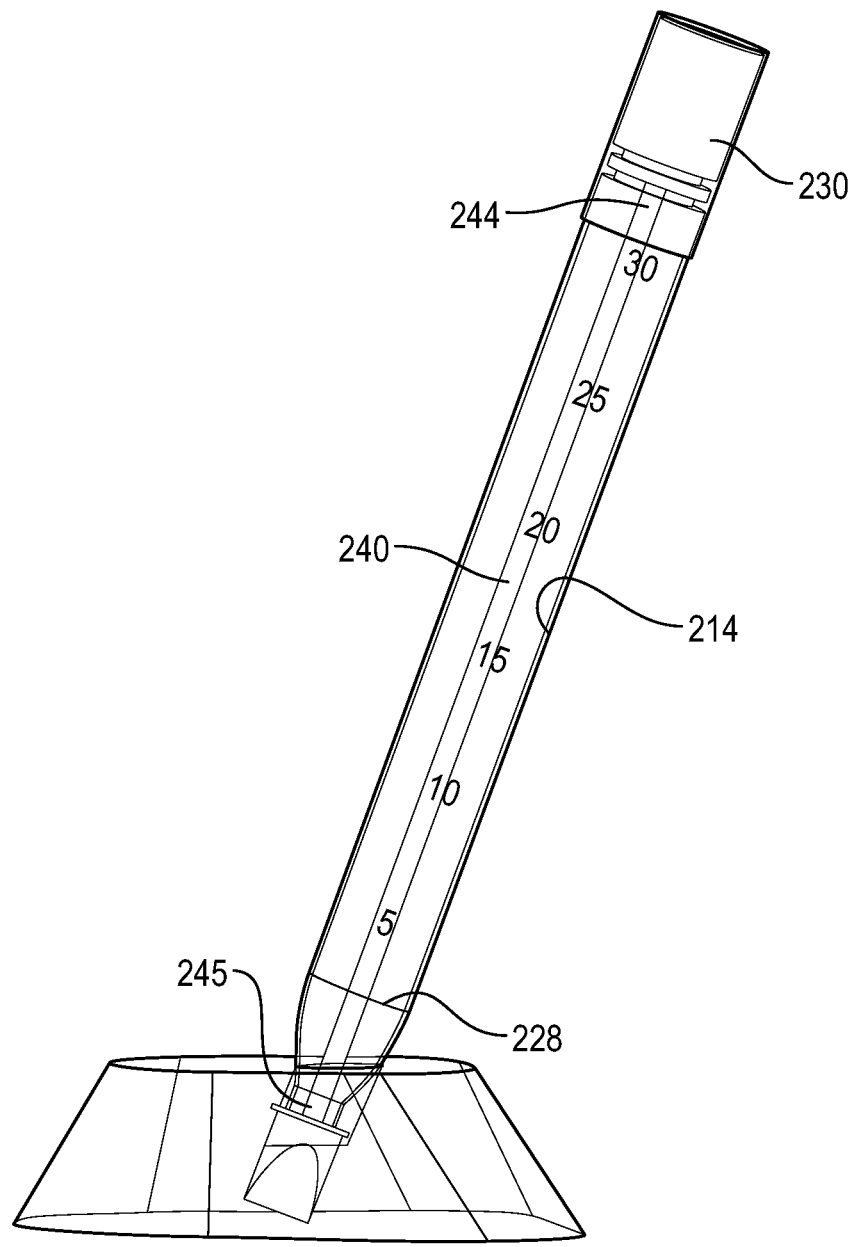
Figure 15D:
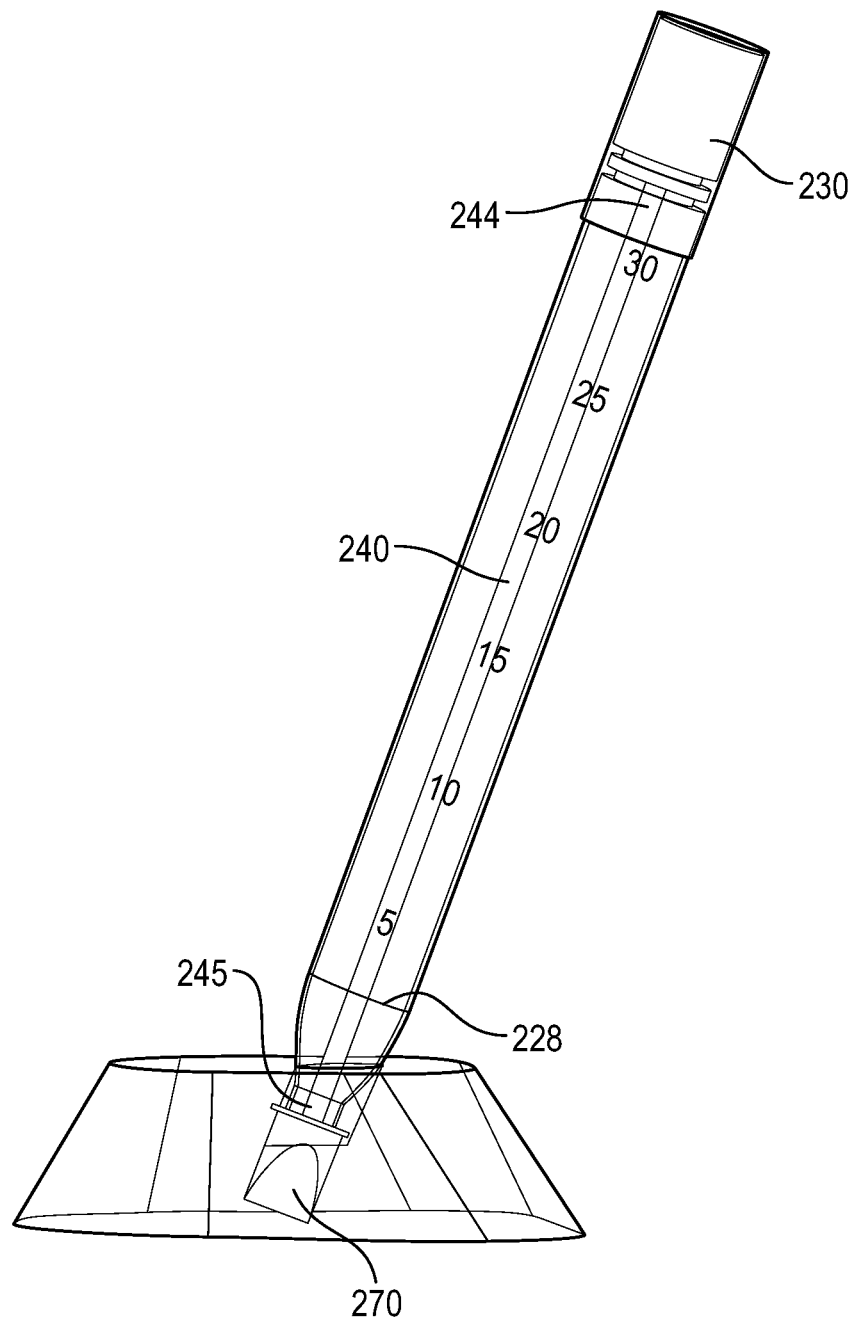

In operation, as shown in FIG. 15A, once the fluid applicator 200 is taken out of primary packaging, the clinician depresses the end press 230 with sufficient force to advance the end press 230 and the push button 242 in a distal direction. As shown in FIG. 15B, upon application of continued depression of the end press 230, the push rod 240 advances toward the one-way valve 270 such that the piercing tip 246 of the push rod 240 pierces open the one-way valve 270 to allow disinfectant 218 to flow out from the chamber 216 in a controlled and constant matter onto the fluid applicator sponge 294. In one or more embodiments, the end press 230 is now pressed similar to a cam or thrust device to push the push rod 240 into the one-way valve 270 to rupture or open the one-way valve 270 creating a passage for the disinfectant 218 to flow into the sponge 294 which gets soaked with fluid disinfectant 218. The side surfaces of the end press 230 are configured to provide a surface onto which distal pressure can be applied in a pinching motion in direction "B" to deform the end press. As shown in FIG. 14, the clinician can control the volume and flow rate of the disinfectant dispensed by applying force to the side walls of the end press in a pinching motion in direction "B" to deform the end press so that additional disinfectant solution located in the chamber flows through the one-way valve onto the sponge 294 to release fluid. As shown in FIG. 15C, releasing the end press causes the push rod 240 to retract such that the piercing tip 246 withdraws from the one-way valve 270 to seal and close the one-way valve 270 to stop further disinfectant 218 from being released onto the fluid applicator sponge 294. As shown in FIG. 15D, the fluid applicator 200 can now be used for skin preparation and disinfection. In one or more embodiments, the end press is deformable and may be pressed on two opposing sides to squeeze disinfectant out of the container with flow control. The user may apply pressure to two sides of the end press using a pinching motion for collapsing a portion of the deformable end press for driving disinfectant out of the chamber 116 by depressing the end press in the direction shown by arrow "B". Hence, the amount of fluid can be precisely controlled directly by the clinician, as to avoid excessive dripping or pooling regardless of desired coverage rate, skin absorption rates and scrubbing force. The deformable end press may be made of elastomeric material, e.g. thermoset rubber, thermoplastic vulcanizate, or thermoplastic elastomers.

The deformable end press may be made of elastomeric material, e.g. thermoset rubber, thermoplastic vulcanizate, or thermoplastic elastomers, natural rubber, synthetic rubber, thermoplastic materials, or other easily disposable and/or recyclable material and combinations thereof. Thermoplastic elastomers include, but are not limited to, polypropylene, polyethylene and the like. Materials should be chosen to be compatible with the solution, medicament and manufacturing process being used.

One or more embodiments, the outer surface of the barrel also includes metering marks that can be configured to gauge how much fluid has been displaced, was actually used on the area.

The device is designed to be compatible in interacting with various disinfectants. In one or more embodiments, the disinfectant or antimicrobial agent may include variations of alcohol or chlorhexidine. The disinfectant or antimicrobial agent may be selected from the group consisting essentially of isopropyl alcohol, ethanol, 2-propanol, butanol, methylparaben, ethylparaben, propylparaben, propyl gallate, butylated hydroxyanisole (BHA), butylated hydroxytoluene, t-butyl-hydroquinone, chloroxylenol, chlorhexidine, chlorhexidine diacetate, chlorohexidine gluconate, povidone iodine, alcohol, dichlorobenzyl alcohol, dehydroacetic acid, hexetidine, triclosan, hydrogen peroxide, colloidal silver, benzethonium chloride, benzalkonium chloride, octenidine, antibiotic, and mixtures thereof. In one or more preferred embodiments, the disinfectant comprises a 2% Chlorhexidine Gluconate (CHG) and 70% Isopropyl Alcohol (IPA) formulation. In one or more embodiments, the disinfectant or antimicrobial agent may be a fluid or a gel.

The fluid applicators disclosed in the present disclosure are low cost with respect to both manufacturing costs and retail cost to the end user based on the number and type of materials used compared to fluid applicators currently in the market.

While the present disclosure has been shown and described with reference to certain exemplary embodiments thereof, it will be understood by those skilled in the art that various changes in form and details may be made therein without departing from the spirit and scope of the embodiments of the present disclosure. Furthermore, any of the features or elements of any exemplary implementations of the embodiments of the present disclosure as described above and illustrated in the drawing figures can be implemented individually or in any combination(s) as would be readily appreciated by skilled artisans without departing from the spirit and scope of the embodiments of the present disclosure.

In addition, the included drawing figures further describe non-limiting examples of implementations of certain exemplary embodiments of the present disclosure and aid in the description of technology associated therewith. Any specific or relative dimensions or measurements provided in the drawings other as noted above are exemplary and not intended to limit the scope or content of the inventive design or methodology as understood by artisans skilled in the relevant field of invention.

Reference throughout this specification to "one embodiment," "certain embodiments," "one or more embodiments" or "an embodiment" means that a particular feature, structure, material, or characteristic described in connection with the embodiment is included in at least one embodiment of the disclosure. Thus, the appearances of the phrases such as "in one or more embodiments," "in certain embodiments," "in one embodiment" or "in an embodiment" in various places throughout this specification are not necessarily referring to the same embodiment of the disclosure. Furthermore, the particular features, structures, materials, or characteristics may be combined in any suitable manner in one or more embodiments.

Although the disclosure herein has provided a description with reference to particular embodiments, it is to be understood that these embodiments are merely illustrative of the principles and applications of the present disclosure. It will be apparent to those skilled in the art that various modifications and variations can be made to the method and apparatus of the present disclosure without departing from the spirit and scope of the disclosure. Thus, it is intended that the present disclosure include modifications and variations that are within the scope of the appended claims and their equivalents.

What is claimed is:

1. A fluid applicator comprising:
   a barrel including a sidewall having an inside surface defining a chamber for retaining a fluid, an open proximal end, a distal end including an elongate tip extending distally therefrom having a passageway therethrough in fluid communication with said chamber and an outlet on the distal end of the barrel;
   an end press disposed on the open proximal end to fluidly seal the open proximal end of the barrel;
   a push rod disposed within the chamber of the barrel, the push rod having a push button disposed on a proximal end of the push rod adjacent to the end press and a piercing tip disposed on a distal end of the push rod;
   a port mounted on the sidewall of the barrel; the port including at least one side wall having an inside surface defining a compartment;
   a hydrophobic filter disposed within the port on the sidewall of the chamber, the hydrophobic filter being in fluid communication with the chamber;
   a cap attached to the port via a hinge;
   a one-way valve disposed on the outlet on the distal end of the barrel;
   a disinfectant or an antimicrobial agent disposed within the chamber between the one-way valve and the end press;
   a housing having a base and an open proximal end; and
   a fluid applicator sponge disposed in the base of the housing, the one-way valve at least partially extending into the base of the housing and embedded into the fluid applicator sponge, the tip and the one-way valve positioned a distance from the open proximal end of the housing.

2. The fluid applicator of claim 1, wherein the one-way valve is a duckbill valve, an umbrella valve, a ball-check valve, diaphragm check valve, swing check valve, stop-check valve, lift-check valve, or a combination thereof.

3. The fluid applicator of claim 2, wherein the one-way valve is a duckbill valve.

4. The fluid applicator of claim 1, wherein the end press is attached internally to the push rod.

5. The fluid applicator of claim 1, wherein the fluid applicator sponge is configured to uniformly distribute disinfectant released from the one-way valve.

6. The fluid applicator of claim 1, wherein the barrel is at an angle relative to the housing.

7. The fluid applicator of claim 1, wherein the compartment of the port surrounds the hydrophobic filter.

8. The fluid applicator of claim 1, wherein the hinge is a living hinge.

9. The fluid applicator of claim 8, wherein the hinge opens between a fully closed position to a fully open position of at least 120 degrees.

10. The fluid applicator of claim 1, wherein the disinfectant or the antimicrobial agent is selected from a group consisting of isopropyl alcohol, ethanol, 2-propanol, butanol, methylparaben, ethylparaben, propylparaben, propyl gallate, butylated hydroxyanisole (BHA), butylated hydroxytoluene, t-butyl-hydroquinone, chloroxylenol, chlorohexidine, chlorhexidine diacetate, chlorohexidine gluconate, povidone iodine, alcohol, dichlorobenzyl alcohol, dehydroacetic acid, hexetidine, triclosan, hydrogen peroxide, colloidal silver, benzethonium chloride, benzalkonium chloride, octenidine, antibiotic, and mixtures thereof.

11. The fluid applicator of claim 1, wherein the barrel comprises a polypropylene or polyethylene material.

12. The fluid applicator of claim 1, further comprising volume scale markings on an outer surface of the barrel.

13. A fluid applicator comprising:
   a barrel including a sidewall having an inside surface defining a chamber for retaining a fluid, an open proximal end, a distal end including an elongate tip extending distally therefrom having a passageway therethrough in fluid communication with said chamber and an outlet on the distal end of the barrel;
   a plurality of volume scale markings on an outer surface of the barrel;
   a deformable end press disposed on the open proximal end to fluidly seal the open proximal end of the barrel;
   a push rod disposed within the chamber, the push rod having a push button disposed on a proximal end of the push rod adjacent to the end press and a piercing tip disposed on a distal end of the push rod;
   a one-way valve disposed on the outlet on the distal end of the barrel;
   a disinfectant or an antimicrobial agent disposed within the chamber between the one-way valve and the end press;
   a housing having a base and an open proximal end; and
   a fluid applicator sponge disposed in the base of the housing, the one-way valve at least partially extending into the base of the housing and embedded into the fluid applicator sponge, the tip and the one-way valve positioned a distance from the open proximal end of the housing.

14. The fluid applicator of claim 13, wherein the one-way valve is a duckbill valve, an umbrella valve, a ball-check valve, diaphragm check valve, swing check valve, stop-check valve, lift-check valve or a combination thereof.

15. The fluid applicator of claim 14, wherein the one-way valve is a duckbill valve.

16. The fluid applicator of claim 13, wherein the fluid applicator sponge is configured to uniformly distribute disinfectant released from the one-way valve.

17. The fluid applicator of claim 13, wherein the barrel is at an angle relative to the housing.

18. The fluid applicator of claim 13, wherein the end press made of elastomeric material.

19. The fluid applicator of claim 13, wherein the disinfectant or the antimicrobial agent is selected from the group consisting essentially of isopropyl alcohol, ethanol, 2-propanol, butanol, methylparaben, ethylparaben, propylparaben, propyl gallate, butylated hydroxyanisole (BHA), butylated hydroxytoluene, t-butyl-hydroquinone, chloroxylenol, chlorhexidine, chlorhexidine diacetate, chlorhexidine gluconate, povidone iodine, alcohol, dichlorobenzyl alcohol, dehydroacetic acid, hexetidine, triclosan, hydrogen peroxide, colloidal silver, benzethonium chloride, benzalkonium chloride, octenidine, antibiotic, and mixtures thereof.

20. The fluid applicator of claim 13, wherein the disinfectant or the antimicrobial agent is a fluid or a gel.

* * * * *